US012678050B2

(12) United States Patent
Hedegaard et al.

(10) Patent No.: US 12,678,050 B2
(45) Date of Patent: Jul. 14, 2026

(54) RAMAN COMPUTED TOMOGRAPHY (RAMAN-CT) SYSTEM AND METHOD

(71) Applicants: Syddansk Universitet, Odense M (DK); King's College London, London (GB)

(72) Inventors: Martin Aage Barsøe Hedegaard, Årslev (DK); Mads Sylvest Bergholt, Croydon (GB); Simon Vilms Pedersen, Odense SØ (DK); Anders Runge Walther, Odense S (DK)

(73) Assignees: Syddansk Universitet, Odense (DK); King's College London, London (GB)

( * ) Notice: Subject to any disclaimer, the term of this patent is extended or adjusted under 35 U.S.C. 154(b) by 0 days.

(21) Appl. No.: 18/975,590

(22) Filed: Dec. 10, 2024

(65) Prior Publication Data

US 2025/0295312 A1  Sep. 25, 2025

Related U.S. Application Data

(63) Continuation of application No. 17/596,724, filed as application No. PCT/EP2020/067127 on Jun. 19, 2020, now abandoned.

(30) Foreign Application Priority Data

Jun. 19, 2019  (EP) ..................................... 19181335

(51) Int. Cl.
A61B 5/00 (2006.01)
(52) U.S. Cl.
CPC .......... A61B 5/0075 (2013.01); A61B 5/0073 (2013.01); A61B 2503/40 (2013.01)
(58) Field of Classification Search
CPC .... A61B 5/0062; A61B 5/0073; A61B 5/0075
See application file for complete search history.

(56) References Cited

U.S. PATENT DOCUMENTS 6,205,353 B1 * 3/2001 Alfano ................. A61B 5/0073
                                                  600/476
2004/0127783 A1 * 7/2004 Kruger ................. A61B 5/0095
                                                  600/407

(Continued)

FOREIGN PATENT DOCUMENTS

CN       108469429 A     8/2018
WO       WO 96/26431 A1  8/1996

OTHER PUBLICATIONS

Chen, Xueli et al., "Volumetric chemical imaging by stimulated Raman projection microscopy and tomography" Nature Communications, Apr. 2017, pp. 1-12, No. 8, vol. 15117.

(Continued)

*Primary Examiner* — Amelie R Davis
(74) *Attorney, Agent, or Firm* — Knobbe, Martens, Olson & Bear LLP

(57) ABSTRACT

The invention relates to an optical tomography scanning system (1) for 3D imaging of an object (100), for example an experimental rodent or a patient, using Raman scattered light from the object. A laser (1) and an optical configuration (2) for fixating the object and arranged for rotation (Θ) is provided, and an optical receiving part (3) receives Raman scattered light. The optical receiving part has a detector array (35) for receiving the Raman scattered light in two spatial dimensions (X, Z), and optical guide means (37) convey Raman scattered light to a spectrometer (38), where multiple spectra are recorded for the two spatial dimensions for each relative rotational position (Θ) of the object. A 3D image reconstruction of the object based on the multiple spectra at a plurality of relative rotational positions (Θ) of the object enables 3D tomographic imaging of the object, such as an experimental rat.

16 Claims, 19 Drawing Sheets
(5 of 19 Drawing Sheet(s) Filed in Color)

(56) References Cited

U.S. PATENT DOCUMENTS

| | | | | |
|---|---|---|---|---|
| 2007/0178067 | A1 | 8/2007 | Maier et al. | |
| 2007/0253908 | A1* | 11/2007 | Rice .................... | A61B 5/0073 |
| | | | | 424/9.4 |
| 2009/0238333 | A1 | 9/2009 | Matousek et al. | |
| 2011/0261354 | A1 | 10/2011 | Sinfield et al. | |
| 2019/0261897 | A1* | 8/2019 | Kersey .............. | A61B 5/14546 |
| 2021/0169333 | A1* | 6/2021 | Zalevsky ............. | A61B 5/0051 |
| 2021/0327107 | A1* | 10/2021 | Behrooz .............. | G06T 11/006 |

OTHER PUBLICATIONS

Demers, Jennifer-Lynn H. et al,. "Multichannel diffuse optical Raman tomography for bone characterization in vivo: a phantom Study" Biomedical Optics Express, Sep. 2012, Vo. 3, No. 9.
Demers, Jennifer-Lynn H. et al,. "Next-generation Raman tomography instrument for non-invasive in vivo bone imaging" Biomedical Optics Express, Mar. 2015, vol. 6, No. 3.
Luo, Xixin et al., "Raman tomography with frequency modulated excitation and spatially coded detection" Proceedings of SPIE, Event: SPIE BiOS, 2019, San Francisco, CA, US, pp. 1-9.
Schulmerich, Matthew V. et al., "Noninvasive Raman tomographic imaging of canine bone tissue" Journal of Biomedical Optics, Mar./Apr. 2008, pp. 020506-1-020506-3, vol. 13, No. 2.
Yan, Tianyu et al., "Raman spectroscopic imaging with frequency modulation based spatially encoded light" Proceedings of SPIE, Event: SPIE BiOS, 2019, San Francisco, CA, US, pp. 1-8.
International Search Report for PCT/EP2020/067127 dated Sep. 11, 2020.
International Preliminary Report on Patentability for PCT/EP2020/067127 dated Dec. 21, 2021.

* cited by examiner

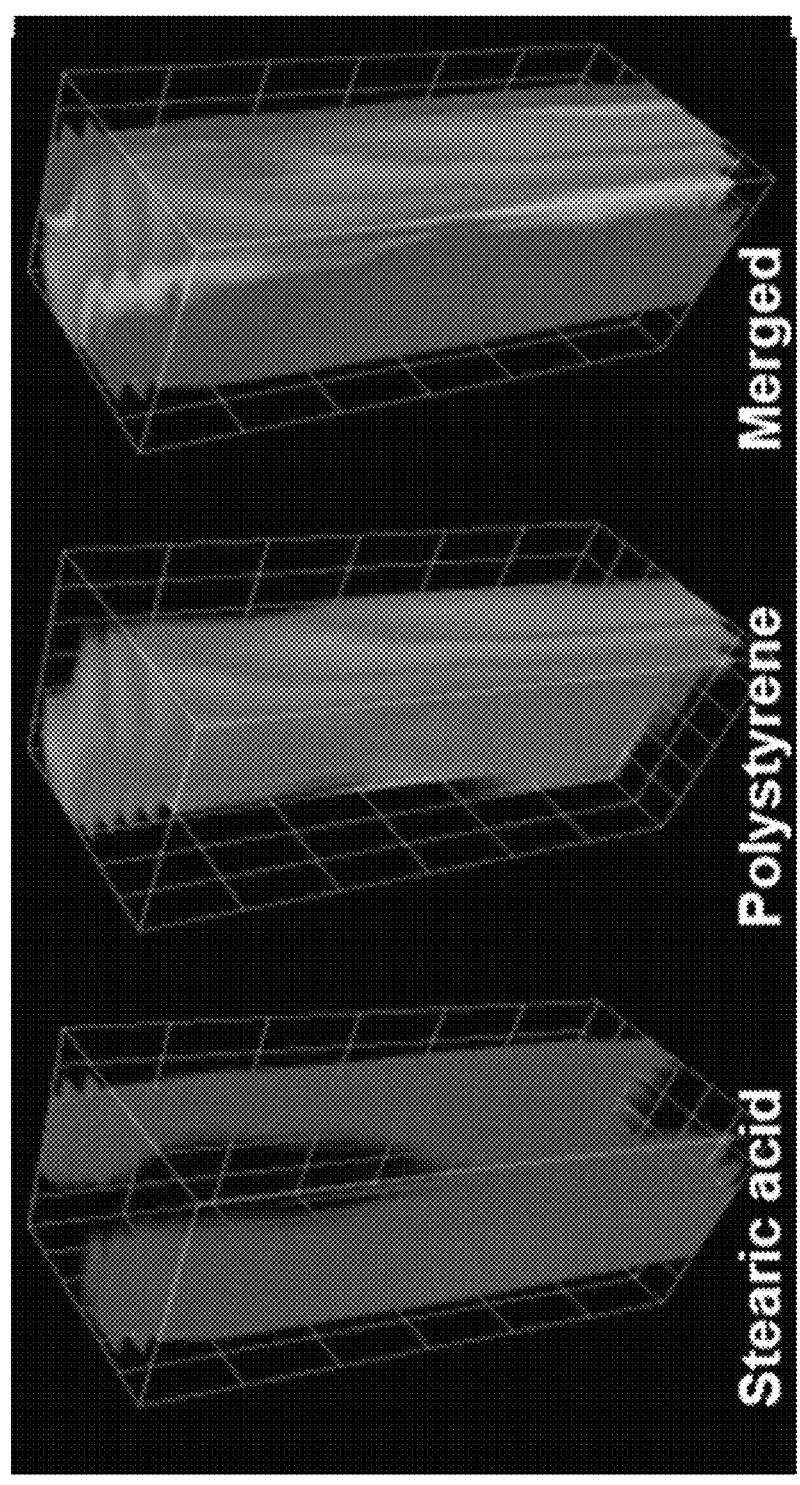
Fig. 8A (full colour)

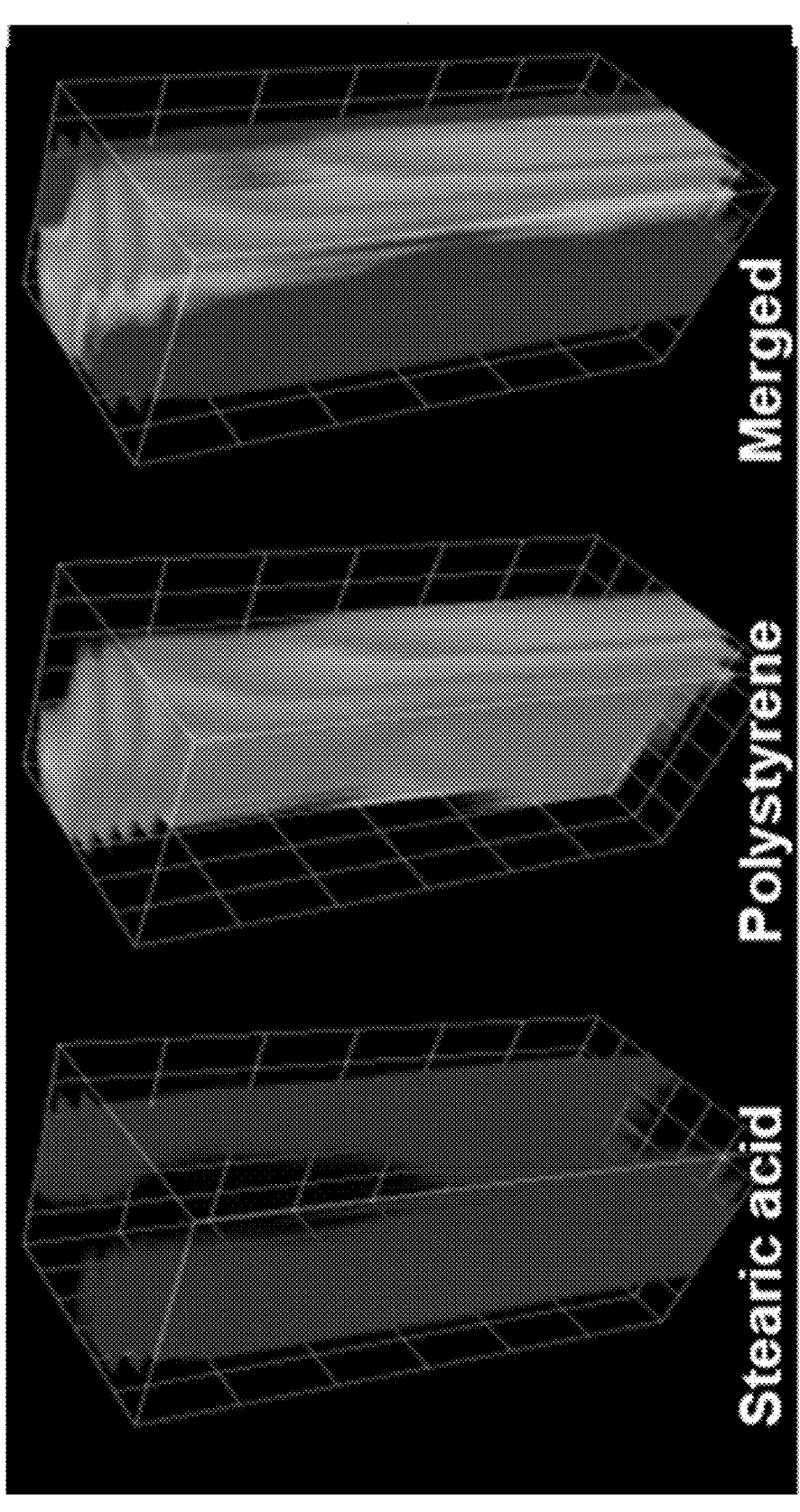
Fig. 8B (grayscale)

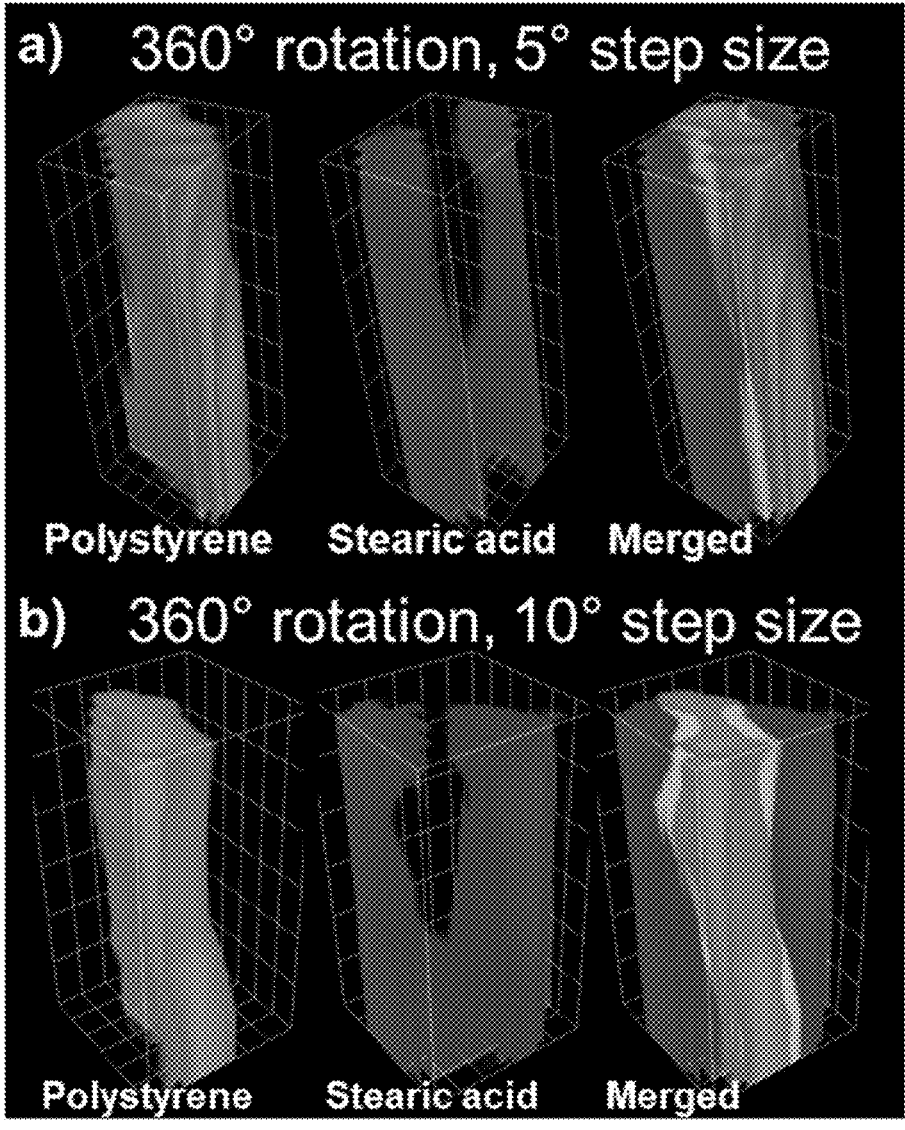
Fig. 10A (full colour)

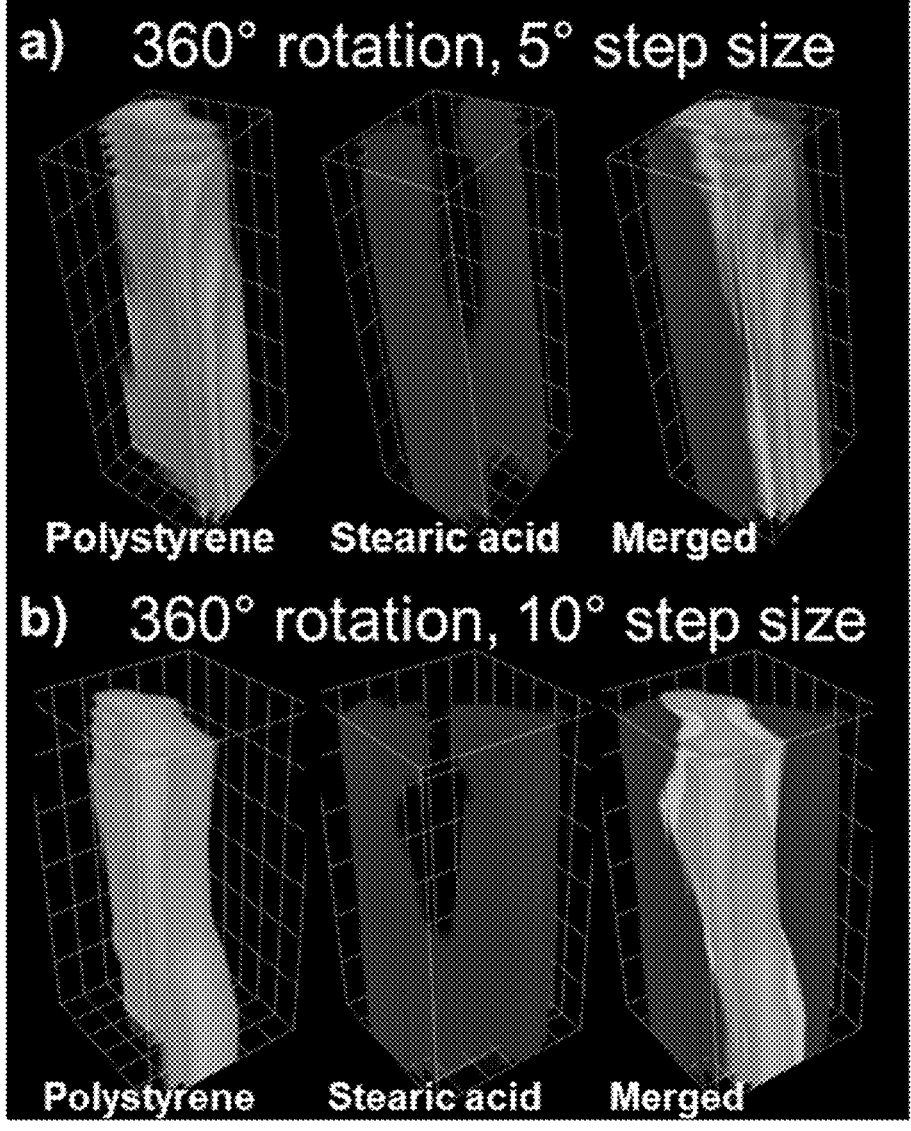
Fig. 10B (grayscale)

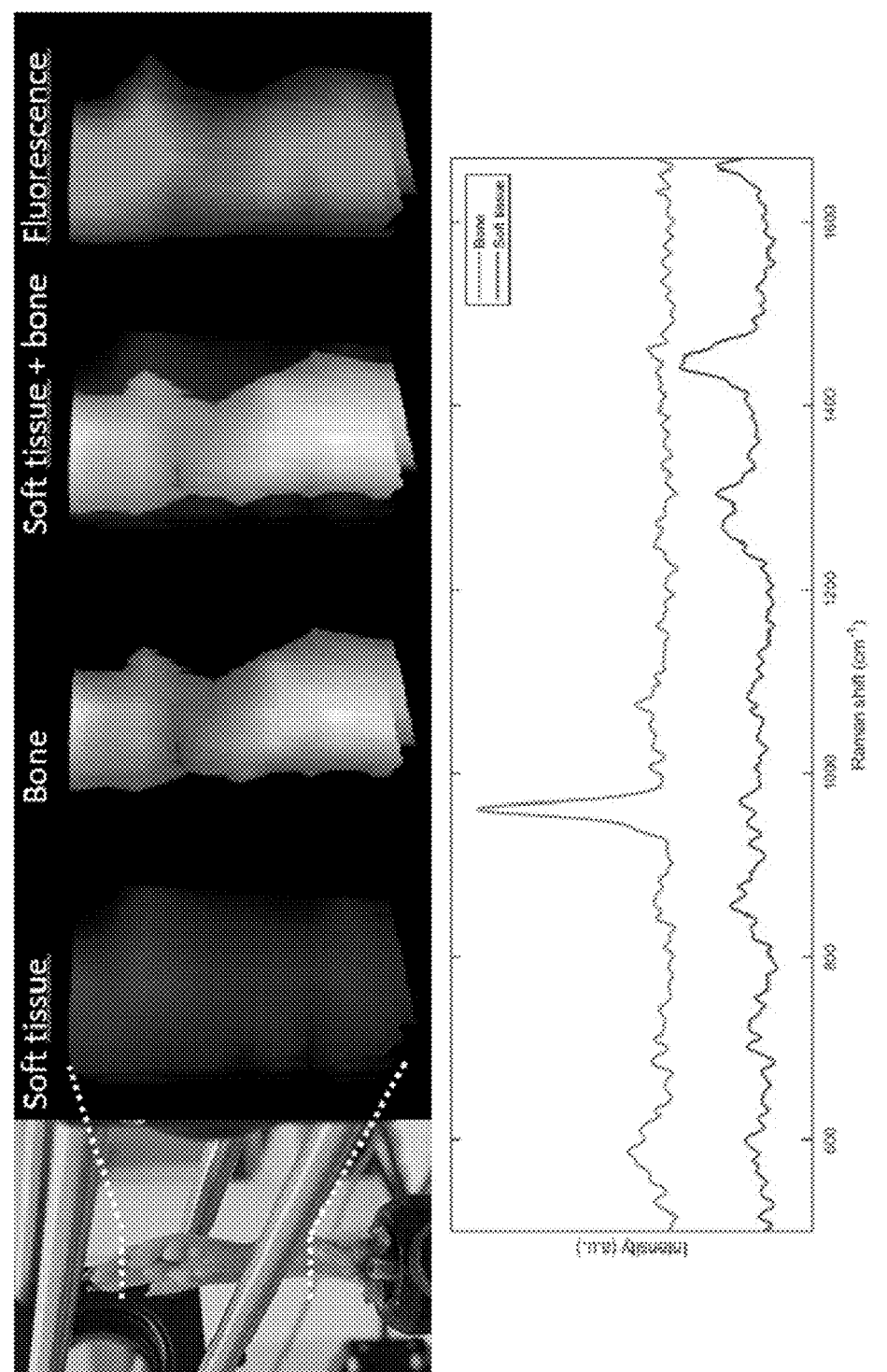
Fig. 13A (full colour)

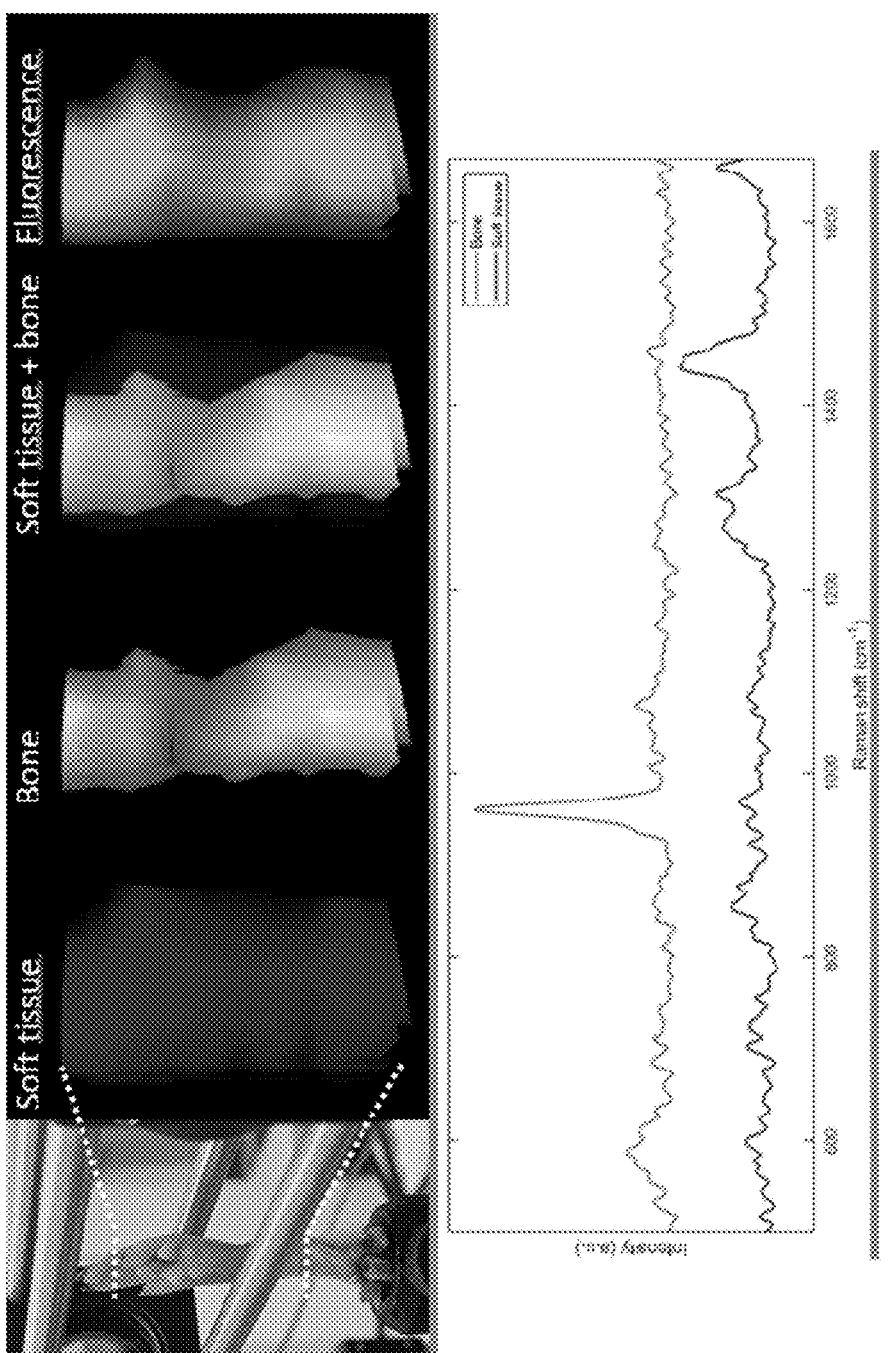
Fig. 13B (grayscale)

1

RAMAN COMPUTED TOMOGRAPHY (RAMAN-CT) SYSTEM AND METHOD

CROSS REFERENCE TO RELATED APPLICATIONS

This application is a continuation of U.S. application Ser. No. 17/596,724, filed on Dec. 16, 2021, which is a U.S. National Phase Application of PCT International Application Number PCT/EP2020/067127, filed on Jun. 19, 2020, designating the United States of America and published in the English language, which is an International Application of and claims the benefit of priority to European Patent Application Ser. No. 19/181,335.1, filed on Jun. 19, 2019. The disclosures of the above-referenced applications are hereby expressly incorporated by reference in their entireties.

FIELD OF THE INVENTION

The present invention relates to a Raman computed tomography (Raman-CT, or just R-CT) system and a corresponding method. Thus, the invention relates to a Raman computed tomography where 3D images can be obtained like with conventional CT images using X-ray or PET. However, the present invention using Raman CT is label-free and does not require injection of any chemical reagents at all. Furthermore, because the invention relies on Raman in-elastic scattering there is obtained a chemical "finger-print" of any embedded materials. This could be especially important for non-invasive clinical diagnostics and for research purposes using e.g. experimental mice for medical testing, and also opens the possibility of using Raman CT for medical imaging and diagnosis of human patients.

BACKGROUND OF THE INVENTION

Tomography is the process of generating cross-sectional images by using penetrating waves such as electromagnetic or acoustic. Tomography is used in a vast verity of scientific areas where cross-sectional images are desired. There are three central tomographic imaging systems within the medical industry; X-ray, MRI, and Ultrasonic. The reconstruction of the image from the system measurements is typically performed using topographical reconstruction (TR) algorithms.

A tomographic imaging system, also known as Computed tomography (CT) system, is a general term for a system which can reconstruct cross-sectional (tomographic) images based on a wide range of measurement techniques. CT systems are widely used within the medical imaging industry, where it acts as a vital tool for the diagnosis of multiple diseases. One of the most commonly used CT system is the X-ray CT (XRCT) scanner, which takes multiple X-ray back-projection (BP) measurements at different angles to reconstruct a tomographic image. The XRCT scanner functions by first emitting X-rays from an X-ray source through the sample and detecting the X-ray attenuation with the detector. The detector consists of an array of detectors used to correlate the detected X-ray with a spatial position on the sample. In another variant, CT can be performed or supplemented by positron emission tomography (PET), but all these CT variants have the disadvantage of exposing the patients to some level of ionizing radiation, which limits and complicate the use of these CT techniques.

Recently, there have been various suggestions for Raman CT, for example from the University of Michigan (USA) and others, cf. by Demers et al., 1 Mar. 2015 I Vol. 6, No. 3 BIOMEDICAL OPTICS EXPRESS, 793, where Raman tomography is obtained in an optical configuration using Raman light from transmission, which unfortunately requires a complex optical collection around the whole object being examined, and at a close distance to the object, so-called contact mode, or near contact mode, with the object, e.g. a body part of a test animal. Thus, this technique is therefore not suitable for up-scaling because it requires a close-fit between the optical configuration and the object being examined. Furthermore, the presented technique generally requires spatial priors, typically in the form of micro-CT imagery, to refine reconstruction of Raman scattering events. This is undesirable for medical purposes, owing to the aforementioned use of ionizing radiation.

US patent application 2009/0238333 (to Science and Technology Facilities Council, UK) discloses another optical system for non-invasive in-vivo measurement of a composition of a tissue within a part (of a human or animal subject), which is carried out by detecting a Raman spectral characteristic in light scattered through the object using a forward transmission. The technique is applied to the detection of calcifications in human breast tissues, but is apparently not applied to obtain 3D tomographic scanning of where exactly the calcification is located in the breast. Likewise, this reference applies a contact mode, or near contact mode, with the object being examined, which makes it complex and difficult to use for other body parts, or for different patients. Also no genuine 3D tomographic scanning of the body part is provided.

International patent application WO 96/26431 discloses a system and a method for using time gated scattered light, for determining the location and composition of material within various organs of the human body. The systems and methods provides for medical imaging in three dimensions of internal body structures for diagnostic purposes. Stationary and scanning fiber optic systems can be used to deliver laser radiation onto the object to be imaged and to collect the time gated information for image reconstruction.

Chinese patent application CN 108 469 429 discloses a two-mode Raman optical projection tomography system. Samples are irradiated by the laser beam after the beam being expanded by beam expander. Sparse sampling method is used for signal collection. Multi-spectral Raman scattering signal acquisition module collects Raman scattering light produced by samples. Background noise is removed from the collected data. Sparse sampling data are reconstructed by using algebraic reconstruction method (ART) based on Total Variation (TV) minimization. The three-dimensional structure image obtained by reconstruction and the three-dimensional chemical compositions image are fused to obtain the three-dimensional volume image with multiple information.

Hence, an improved Raman computed tomography (Raman-CT) system would be advantageous, and in particular a more efficient and/or flexible Raman CT system would be advantageous.

OBJECT OF THE INVENTION

It is a further object of the present invention to provide an alternative to the prior art.

In particular, it may be seen as an object of the present invention to provide a more efficient and/or flexible Raman CT system that solves the above mentioned problems of the prior art with imaging at some distance from the object and still providing quickly and reliably tomographic 3D images of an object, in particular a macroscopic object, such as a patient or an animal, or body parts of a patient or an animal, and avoiding the use of spatial priors obtained through techniques such as micro-CT, involving use of ionizing radiation.

SUMMARY OF THE INVENTION

Thus, the above described object and several other objects are intended to be obtained in a first aspect of the invention by providing an optical tomography scanning system for 3D imaging of an associated object, such as non-invasive 3D imaging of, at least part of, a patient or an animal, using Raman scattered light from said object, said system comprising:

a monochromatic light source arranged for illuminating said object, an optical configuration for fixating said object and arranged for rotating to a plurality of relative rotational positions ($\Theta$) between said object and the optical tomography scanning system, an optical receiving part optically arranged relative to said object for receiving Raman scattered light from said object, the optical receiving part comprising:

a detector array arranged for receiving the Raman scattered light in two spatial dimensions (X, Z), and a plurality of optical guide means arranged for receiving and conveying further said Raman scattered light to a spectrometer for recording into multiple spectra upon acquiring in said two spatial dimensions for each relative rotational position of said object, and a processing part arranged for 3D image reconstruction of said object based on said recorded multiple spectra based on a plurality of relative rotational positions ($\Theta$) of said object, and the scattered light from said object detected by said optical receiving part displays an anisotropic polar plot as a function of said relative rotational position ($\Theta$) corresponding to the internal spatial structure of said object.

The invention is particularly, but not exclusively, advantageous for obtaining an improved Raman CT system capable of providing 3D tomographic imaging of a macroscopic object in a quick and efficient manner, not hitherto considered possible in the field of tomographic imaging using the Raman effect. Thus, the inventors have implemented a fully working operational Raman CT system capable of providing 3D images of a macroscopic object in less than five minutes, such as less than four minutes, less than three minutes, less than two minutes, less than one minute, having a sub-centimetre spatial resolution, such as sub-millimetre resolution, such as resolution of several hundreds of micrometres, such as resolution of one, or more, tens of micrometres, including corresponding spectral information. This is possible without having to use additional CT techniques. Thus, often spectral Raman often is complemented by additional CT technique or means, such as X-ray CT, but this is not necessary with the present invention.

It is noteworthy that the Raman scattered light may be used for objects, such as macroscopic objects, e.g. having a volume of several cubic centimetres and upwards, because often the penetration depth of the excitation light for Raman, e.g. a laser, is considered too low to obtain valuable spatial information from a macroscopic object, and correspondingly the Raman scattered light would be considered to be predominately diffusive, i.e. multiple times scattered, and therefore the spatial information may be at least partly lost during the multiple scattering out of the macroscopic object. However, the present invention convincingly demonstrates that Raman CT of macroscopic objects is indeed possible and thus facilitates new applications of Raman CT, where this was considered not possible, e.g. 3D tomographic imaging of macroscopic objects for example in quality control of industrial objects not visibly transparent, medical 3D tomographic imaging of test animals, or parts thereof, such as mice, rats, rabbits, monkeys, etc., and human patients, such as body parts, like hands, arms, legs, torso, head, etc.

It is contemplated that the traditional approach of considering Raman scattering in a single molecule approach, e.g. in a gas or liquid phase, may have hitherto discouraged work in this direction, cf. Raman Spectroscopy for Chemical Analysis by Richard L. Mccreery, 2000, John Wiley & Sons, for example in Chapters 2 and 3 assuming a uniform Raman scattering. Thus, the present invention shows that Raman spectra and spatial information therefrom can be measured at a relatively large distance away from the macroscopic object being examined, i.e. utilising a free-space optical set-up, which by some would not be expected possible in this technical field.

In the context of the present invention, in particular when used in tomography of living animals and humans, the tomographic technique may be considered 'non-invasive' in the sense that power intensity is adjusted so that laser light irradiance will comply with the European laser regulation (for example IEC/EN 60825, Edition 1.2, 2001-08), especially not exceeding the maximum permissible exposure limit.

Thus for a relatively long wavelength of monochromatic light source, e.g. a laser operating at 785 nm (red) it is possible to operate non-invasively and still have satisfactory signal to noise ratio. As mentioned above, the possible non-invasive character of Raman CT provides a significant advantage over conventional X-ray CT and PET tomography, where radiation levels must be considered for health concern of the patients. Thus, the present invention will typically apply a laser exposure below appropriate safety health limits and thereby effectively being non-invasive for animals and humans.

In the context of the present invention, it is preferred to detect Stoke scattered Raman light from the sample, but in some embodiments, alternatively or additionally, the anti-Stoke scattered Raman light may be detected, for example if the temperature dependency is a relevant consideration.

In advantageous embodiments, the scattered light from said object detected by said optical receiving part may display, or have, constructive interference near, or at, the detector array, preferably said detector array being located approximately at least 5, 10, 15, 20, 25, 30 cm from said object. Thus, it is contemplated, but without being limited to any specific theory or explanation, that in this non-contact mode of operation, the Raman scattered light will for certain angular positions have constructive interference as suggested by the anisotropic, or inhomogeneous, polar plot shown in the detailed description below. The constructive interference may be caused by the spatial structure, in particular the internal spatial structure, of the object being tomographically imaged. Thus, quite differently from, for example, the research mentioned above from the University of Michigan by Demers et al., it is not necessary to have the collection optics very close to the object being imaged for lowering the solid angle of detection like a traditional optical approach would suggest. On the contrary, the teaching and principle of the present invention convincingly demonstrates that a far-field approach is quite possible and also easier to implement in practise.

Thus, the scattered light from said object detected by said optical receiving part may display an anisotropic polar plot as a function of said relative rotational position ($\Theta$) corresponding to the internal spatial structure of said object. Thus, non-isotropic or non-homogenous polar scattering plots are the somewhat surprising result of the present invention. In the context of the present invention, the term 'anisotropic' may be considered the property of being directionally dependent, which implies different properties, in particular different optical properties in different spatial directions, as opposed to isotropy. It can likewise be defined as a difference, when measured along different axes, in a material's physical or optical properties (absorbance, refractive index, etc.).

Raman spectra can be analysed either based on the intensity on a single peak (univariate analysis) or based on complex relationships between intensities of all, or most of, the peaks in the Raman spectrum at once (multivariate analysis). Multivariate analysis allows robust quantitative or semiquantitative assessment of the individual components. This is particular important for complex biomedical Raman spectra of tissues and cells where the spectra of myriads of different molecules are overlapping.

Multivariate analysis may be used to address the situations where multiple measurements are made on each experimental unit and the relations among these measurements and their structures are important. In this application multivariate analysis may be performed on multivariate spectral data. The multivariate spectral data are the multiple full high resolution spectra recorded. Multivariate analysis may be significant in order to extract quantitative chemical information.

The present invention do record spectra at different rotational positions of said object, however the present invention do not use time-gated scattered-light to record a spectrum and is therefore not using time resolved Raman scattering as in WO 96/26431. The present invention records a spectrum using flexible Raman-CT for directly recording of a full high resolution Raman spectrum at each given rotational position. Therefore, when recording into multiple spectra upon acquiring in said two spatial dimensions for each relative rotational position of said object, it is to be understood that the recording of each spectrum of the multiple spectra may be done for a sampling time, but only the spectrum is recorded, no change over time is recorded. The sampling time may be defined as the time needed to sample sufficient data to get a sufficient detailed spectrum.

The present invention records full, or nearly full, high resolution Raman spectra between a minimum and a maximum Raman shift. The full high resolution Raman spectrum between a minimum and a maximum Raman shift may be used in performing multivariate analysis of the recorded Raman spectra. To record the full high resolution Raman spectra may be understood as the frequencies of the Raman scattered light are not altered between the signal leaves the object and the Raman spectra are recorded. Not altered is to be understood as not changed or manipulated, no frequencies are removed and no background noise is removed.

Spectral resolution is critical in Raman spectroscopy to achieve chemical specificity. For detection, CN 108 469 429 utilises an acousto-optic tuneable filter (AOTF). AOTFs have spectral resolution of 16-50 cm−1 and are not using multivariate analysis can therefore not be used to resolve Raman peaks in biomedicine (often <10 cm−1 peak widths) (REF: Raman spectroscopy in Chemical Analysis, Mccreery 2000).

In contrast, the present invention may use multivariate analysis and utilises a high resolution spectrograph that is able to resolve biological Raman peaks (<10 cm−1 peak width). Further, by using a multiplexed acquisition one is still able to rapidly obtain multiple full high resolution Raman spectra (without scanning). This is important to increase imaging speed and preserve resolution and chemical specificity.

In some embodiments, the said optical configuration for fixating said object may be further arranged for performing a relative longitudinal displacement (called z-direction the detailed description below) of said object, said longitudinal displacement being substantially orthogonal to a rotational plane of said relative rotation ($\Theta$) between said object and the optical tomography scanning system, as it would be understood in a cylinder-symmetrical optical configuration. It is to be understood that the longitudinal displacement is relative in the sense that the object being imaged can be displace alone, or the optical tomography scanning system itself, or at least parts thereof, can be displaced relative to the object being imaged, or a combination thereof where both the object and the optical tomography scanning system itself, or at least parts thereof, can be displaced to perform the tomography scanning.

In other embodiments, the tomography scanning of the present invention may simultaneously be obtaining corresponding spectral information and spatial information about said object due to the Raman scattered light containing both the chemical 'fingerprints' of the object and the spatial 'fingerprint' of the object, too, which is quite different from much of the previous work in this field where Raman spectroscopy is often just a supplement to spatial information from e.g. X-ray CT or other tomography techniques.

In some embodiments, the tomography scanning may be based on backward-projection (BP) type measurements of the Raman scattered light in said optical receiving part, which is also quite different from much previous work using the Raman reflected light, for example in a traditional confocal microscopic configuration with Raman spectroscopy. Nevertheless, the present invention demonstrates that BP type measurements of the Raman scattered light is feasible and highly useful for fast and reliable tomographic imaging of objects, such as experimental mice or rats. It is further contemplated that the Raman scattered light from said object being detected by said optical receiving part may be forwarded scattered, i.e. a single time scattered in the forward direction, which is quite different from other optical techniques where diffusive photons are measured, i.e. photons that are multiple times scattered.

However, it may alternatively be in a back scattered optical configuration with the light source and the optical receiving part on the same side of the object being imaged. This may work but likely with lower intensity (worse signal to noise ratio) as expected from classical scattering principles, in particular with a complex geometry of the object, e.g. human body (or parts thereof) being relatively difficult to access and measure.

When the optical configuration for fixating said object is further arranged for performing a relative longitudinal displacement (called Z-direction the detailed description below) of said object, said longitudinal displacement being substantially orthogonal to a rotational plane of said relative rotation ($\Theta$) between said object and the optical tomography scanning system, as it would be understood in a cylinder-symmetrical optical configuration, the detector array may be a so-called 'line array' as the skilled person in optics will understand, where the plurality of optical guide means, e.g. a number of optical fibres, are arranged substantially in a rotational plane ($\Theta$) of the object. This may facilitate faster tomographic imaging because the number of optical fibres may acquire Raman spectra in parallel.

In alternative embodiments, the detector array may be a point-like array where an additional scanning (X) in a rotational plane ($\Theta$) of the object is performed for acquiring multiple spectra in said two spatial dimensions. While this is may require more sampling time as the X-dimension is being scanned, it may for some applications be an advantage with the exact same collection fibre is being used for receiving the Raman spectra.

In other embodiments, the detector array may be a two-dimensional detector array wherein Raman scattered light from said object is being detected by said optical receiving part by simultaneous detection in both said rotational plane ($0$) and in an orthogonal (Z) dimension to said rotational plane, i.e. with a two-dimensional detector array, cf. for example FIG. 4 below. Thus, it may enable faster acquisition, but with somewhat more complex collection optics, which could nevertheless be relevant with for example a large or full patient scanning etc. where sampling time must be as quick as possible.

Preferably, the detector array and the corresponding optical guide means may be mutually arranged for conveying a text where the 3D image reconstruction is performed using: a spectral unmixing technique, a spectral Library supervised reconstruction, an information entropy minimization technique, such as BTEM (band target entropy minimization, cf. detailed description below), a multivariate curve resolution (MCR) technique, a vertex component analysis (VCA) technique, N-FINDR, a principal component analysis (PCA) technique, or any combinations thereof as the skilled person on 3D reconstruction will readily understand once the teaching and principle of the present invention is appreciated. Thus, generally regression analysis afterwards followed by individual fitting of each voxel can advantageously be performed. All the here mentioned techniques are commonly known for using multivariate analysis. In particular, the present invention has enabled that an animal body or a patient body, or part thereof, and the 3D image reconstruction may be capable of resolving said spectral information and spatial information to provide a tissue differentiating resolution in the 3D image construction. Thus, a rat leg has been successfully imaged; cf. FIG. 11 and corresponding description below.

The below table summarizes the advantages of the present invention exploiting Raman CT (R-CT) relative to the state-of the-art, especially in relation to animal models:

| State-of-the-art | Current Limitations | Need |
|---|---|---|
| Callipers Plethysmometry Computed tomography (X-ray) Magnetic Resonance Imaging | Conventional calliper and plethysmometry offers no biomolecular information CT and MRI does not offer sensitivity to for example anti-arthritic treatment below 21 days in animal models There exist good techniques for temporal monitoring of for example anti-arthritis compounds | Early sensitive temporal molecular monitoring in animal models Reduction in animal used for experiments and within animal-repeated Shortening late disease duration Higher sensitivity to cartilage erosion Minimisation of animal suffering and improving animal welfare |
| R-CT breakthrough approach: beyond state-of-the-art | | |
| Forward scattering based Raman spectroscopy analogous to CT X-Ray absorption imaging Raman computed tomography (R-CT) for 3D reconstruction of joints at the molecular level Novel integration of spectral unmixing and backprojection reconstruction of molecular species Label-free, non-ionizing, noninvasive imaging technique | | |
| Academic Impact | 3R Impact | Industry Impact |
| We have opened a new technology field of forward scattered R-CT This will create the basis for new research across other scientific disciplines (biomedicine and clinical research) | Use of non-ionising radiation Shorter study duration and reduced severity of end points reduce animal numbers Less pain to the animal More data-rich information generated regarding the cartilage and bone Reduction in the number of animals by up to a factor of 10 due to longitudinal measurements | Economic savings for animal experiments More rapid and robust screening of drug efficacy |

Raman spectrum in each optical guide means, preferably each optical guide means comprises an optical fiber capable of conveying a Raman spectrum from said object so as to enable parallel acquisition of spectra, and thereby facilitate fast scanning.

The optical tomography scanning system according to the present invention may be advantageously applied in a con- '3R' is an abbreviation for replacement, refinement and reduction of test animals in research.

In a second aspect, the present invention relates to a method for optical tomography scanning for 3D imaging of an object, such as non-invasive 3D imaging of, at least part of, a patient or an animal, using Raman scattered light from said object, said method comprising:

providing a monochromatic light source arranged for illuminating said object, fixating in an optical configuration said object, said optical configuration being arranged for rotating to a plurality of relative rotational positions ($\Theta$) between said object and the optical tomography scanning system, arranging an optical receiving part optically relative to said object for receiving Raman scattered light from said object, the optical receiving part comprising:

a detector array arranged for receiving the Raman scattered light in two spatial dimensions, and a plurality of optical guide means arranged for receiving and conveying further said Raman scattered light to a spectrometer for recording into multiple spectra upon acquiring in said two spatial dimensions for each relative rotational position ($\Theta$) of said object, and providing a processing part for 3D image reconstruction of said object based on said recorded multiple spectra based on a plurality of relative rotational positions ($\Theta$) of said object, and the scattered light from said object detected by said optical receiving part displays an anisotropic polar plot as a function of said relative rotational position ($\Theta$) corresponding to the internal spatial structure of said object.

In another aspect of the invention there is provided an optical tomography scanning system for 2D (two-dimensional) imaging of an associated object, such as non-invasive 2D imaging of, at least part of, a patient or an animal, using Raman scattered light from said object, said system comprising:

a monochromatic light source arranged for illuminating said object, an optical configuration for fixating said object and arranged for rotating to a plurality of relative rotational positions ($\Theta$) between said object and the optical tomography scanning system, an optical receiving part optically arranged relative to said object for receiving Raman scattered light from said object, the optical receiving part comprising:

a detector array arranged for receiving the Raman scattered light in one spatial dimension, and a plurality of optical guide means arranged for receiving and conveying further said Raman scattered light to a spectrometer for recording into multiple spectra upon acquiring in said one spatial dimensions for each relative rotational position ($\Theta$) of said object, and a processing part arranged for 2D image reconstruction of said object based on said recorded multiple spectra based on a plurality of relative rotational positions ($\Theta$) of said object.

The invention is particularly, but not exclusively, advantageous for obtaining an improved Raman CT system capable of providing 2D tomographic imaging of a macroscopic object in a quick and efficient manner, not hitherto considered possible in the field of tomographic imaging using the Raman effect, where only a 2D image, i.e. a cross-sectional image of an object, is necessary or sufficient. For example, in quality control of some industrial objects after manufacturing and/or after transport, or for some kind of medical imaging where just one cross-sectional view may be sufficient for medical purposes or diagnostic.

In another aspect, the invention relates to a computer program product being adapted to enable a computer system comprising at least one computer having data storage means in connection therewith to control an optical Raman CT system according to the first aspect, or other aspects, of the invention, such as a computer program product comprising instructions which, when the program is executed by a computer, cause the computer to carry out the method of second aspect of the invention.

This aspect of the invention is particularly, but not exclusively, advantageous in that the present invention may be accomplished by a computer program product enabling a computer system to carry out the operations of the optical system of the first aspect of the invention when down- or uploaded into the computer system. Such a computer program product may be provided on any kind of computer readable medium, or through a network. In particular, the processing part of the invention may be implemented using a computer system.

The individual aspects of the present invention may each be combined with any of the other aspects. These and other aspects of the invention will be apparent from the following description with reference to the described embodiments.

BRIEF DESCRIPTION OF THE FIGURES

The patent or application file contains at least one drawing executed in color. Copies of this patent or patent application publication with color drawing(s) will be provided by the Office upon request and payment of the necessary fee.

The Raman CT system according to the invention will now be described in more detail with regard to the accompanying figures. The figures show one way of implementing the present invention and is not to be construed as being limiting to other possible embodiments falling within the scope of the attached claim set.

FIGS. 8A and 8B show the 3D reconstructed tomographic image of the phantom, FIGS. 10A and 10B show the 3D reconstructed tomographic image of the phantom like in FIGS. 8A and 8B with two polar stepping angles of 5 and 10 degrees, respectively.

FIGS. 13A and 13B show a 3D reconstructed tomographic images from a rat leg.

DETAILED DESCRIPTION OF AN EMBODIMENT

Figure 1:
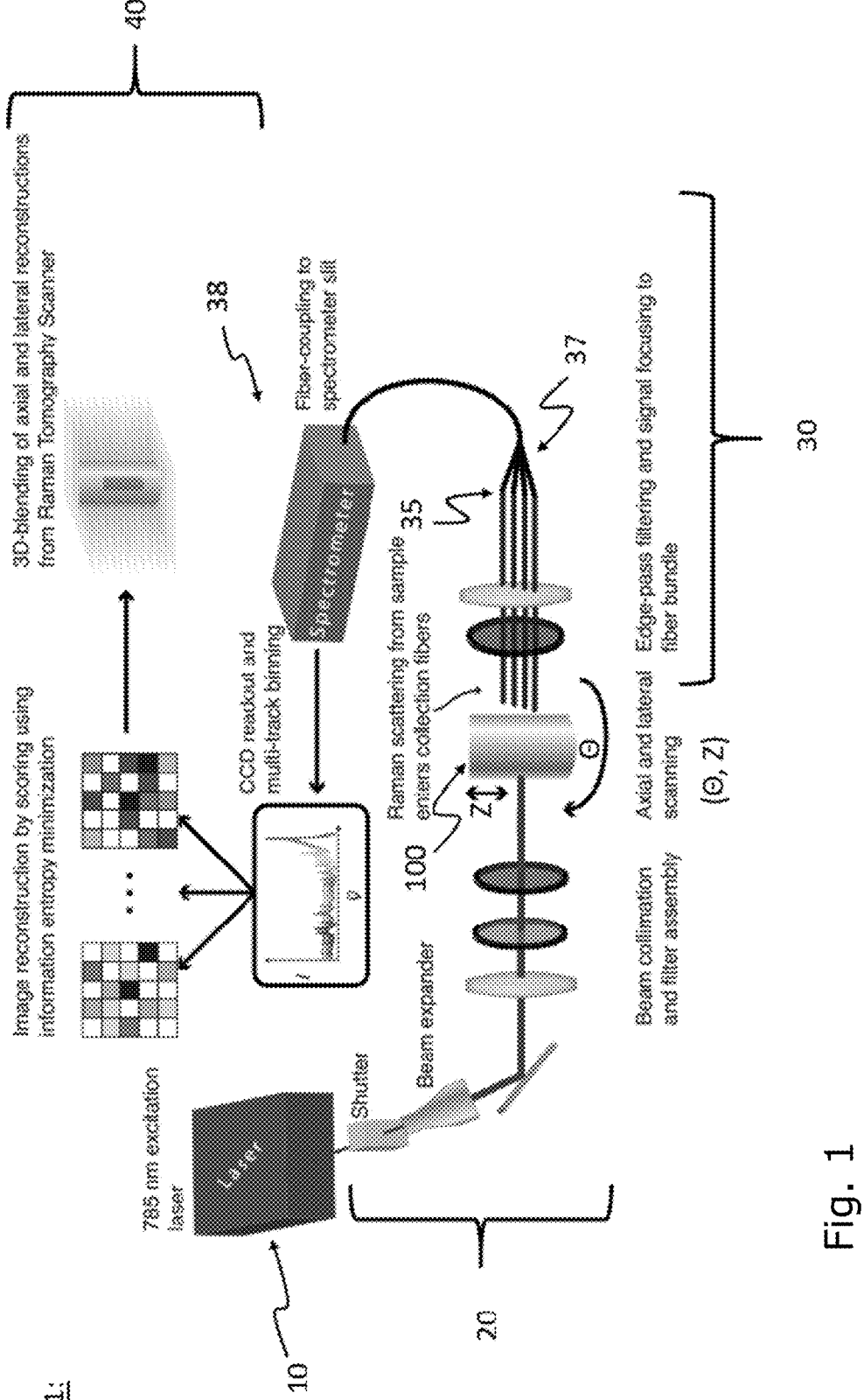
FIG. 1 shows a schematic optical system for Raman CT according to the present invention.

FIG. 1 shows a schematic optical system 1 for Raman CT (R-CT) according to the present invention. The optical tomography scanning system 1 is arranged for 3D imaging of an associated object 100 (shown here just a phantom cylinder). In one embodiment it may be non-invasive 3D imaging of a patient/animal, e.g. a leg or a hand or other body part of such a patient/animal, by using Raman scattered light from said patient.

The R-CT system 1 comprises a monochromatic light source 10, such as a laser, such as a red laser, arranged for illuminating said object 100. An optical configuration 20 with a shutter and a beam expander is capable of fixating the object 10, e.g. on a support, a frame or a rotation stage, and arranged for rotating to a plurality of relative rotational positions Θ between the object and the optical tomography scanning system 1. Thus, by relative rotations the object 100 alone may be rotated or the entire optical system 1 alone may be rotated, the latter being for example suitable for patient imaging on a large scale similarly to conventional X-ray CT systems, or both the object and the optical system may be rotated in some embodiments.

An optical receiving part 30 is optically arranged relative to said object for receiving Raman scattered light from said object 100, the optical receiving part comprises in particular a detector array 35 arranged for receiving the Raman scattered light in two spatial dimensions, e.g. in the lateral dimension Z and across the detector array 35, and a plurality of optical guide means 37, such as optical fibres, are arranged for receiving and conveying further said Raman scattered light to a spectrometer 38 for recording into multiple spectra upon acquiring in said two spatial dimensions for each relative rotational position Θ of said object. Thus, for each rotational position with a given value of Θ, spectra are recorded by the CCD of spectrometer 38 guided thereto by the multiple optical guide means and this may be performed in various lateral positions of Z.

Finally, a processing part 40, such as a dedicated computer system therefore, is arranged for 3D image reconstruction of said object 100 based on these recorded multiple spectra from a plurality of relative rotational positions Θ of the object and the optical system 1 for R-CT.

In some embodiments, rotational scan is performed in steps of 5 or 10 degrees, but depending on the balance between spatial resolution and time spend for measurements, other steps could be 1, 2, 3, or degrees, but also large steps like 15, 20, 30, or degrees could be applied during a full rotation of measurements.

In some embodiments, it is also possible to perform only a part of the full circle rotation of Θ, i.e. 120, 180 or 270 degrees, at the expense of spatial resolution but reducing measurement time, for example if some knowledge is available of the expected spatial structure.

Figure 2A:
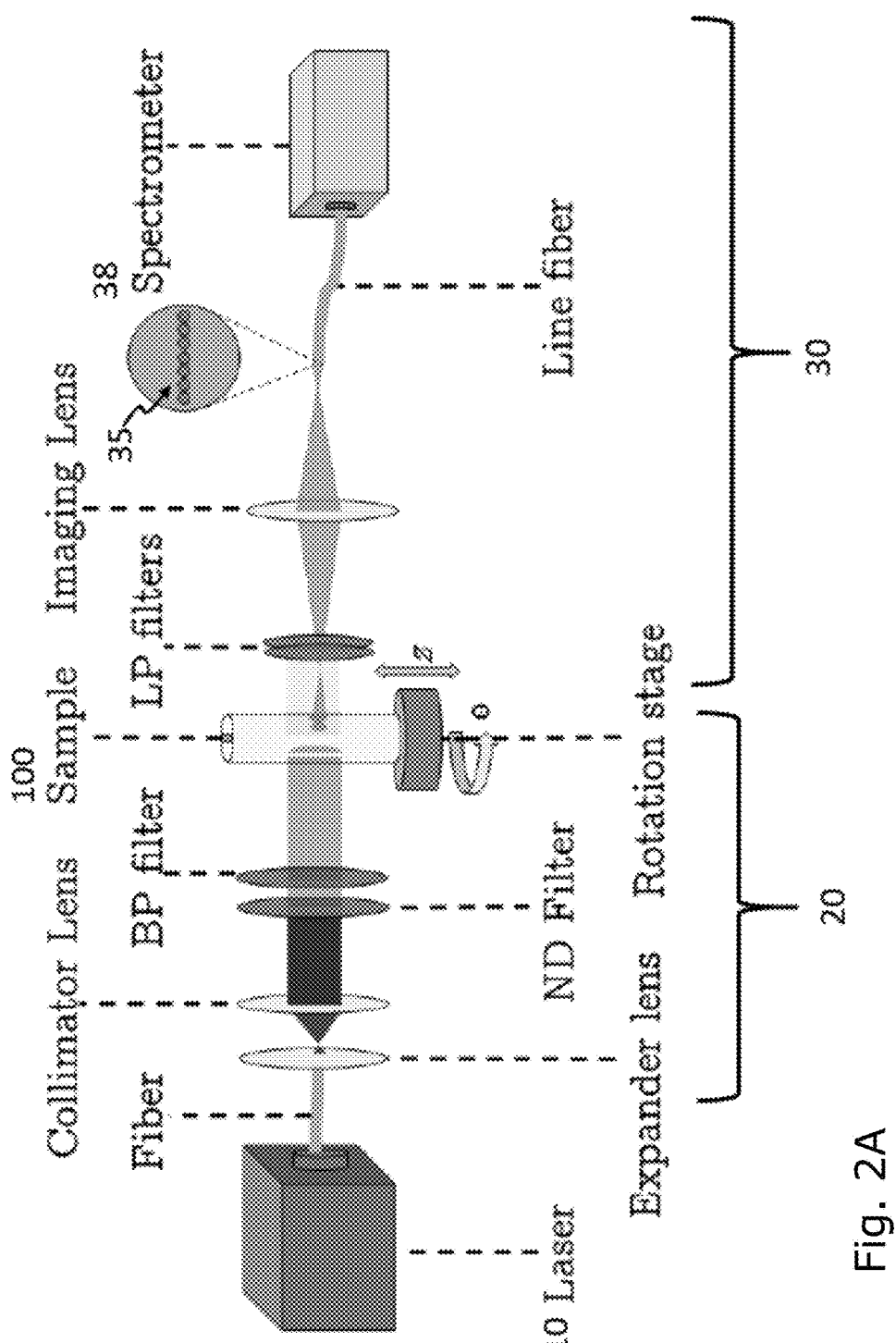
FIGS. 2A and 2B show another schematic optical system for Raman CT according to the present invention with a plurality of optical guide means.

FIG. 2A shows another schematic optical system for Raman CT according to the present invention with a plurality of optical guide means similar to FIG. 1. The optical tomography scanning system shown has a detector array, which is a so-called line array with a linear arrangement of the optical guide means side by side, wherein the plurality of optical guide means, such as seven optical fibres as shown, are arranged substantially in a rotational plane Θ of the object. The detector array measures for each angle, and it measures the Raman signal at multiple points of the sample or object at the same time.

Thus, the laser excitation beam consecutively illuminates the entire sample volume while seven optical fibre collect the Raman scattering across the entire sample. After the scan is finished, the sample is rotated relative, such as to the detector side, and the process is repeated. After a full rotation, the sample is moved up (lateral Z-direction), and the process is repeated. Only the measured Raman scattering is shown in this figure.

The system is constructed within the THORLABS optical cage system, which gives improved control over the rotation and positioning of the optical components. A 785 nm+/−5 nm laser beam, of 450 mW, is passed through a 0.5 m long optical fibre (NA=0.22, Multimode core 100 micrometer). The laser beam is transmitted from the fibre through a beam expander. From the beam expander, the laser beam is passed through an ND filter (OD=6, B-coated) resulting in an excitation beam power of 155 mW. The laser beam is then passed through a band pass filter (Blocking band, OD=3 to OD=5, FWHM=17:1 nm, center wavelength 785 nm) which acts as a laser clean-up filter used to remove vibrational components from the laser, outside the desired excitation wavelength. Following the ND filter, the beam illuminates the sample, and Raman scattering is generated. The Raman scattering on the opposite side of the sample is passed through two long pass filters with an edge wavelength of 805 nm (OD>6 for 624-790 nm) and a transmission width of 19.8 nm to attenuate the intensity at the excitation wavelength. Two filters were used to increase the filter attenuation. Following, the Raman-scattered light is transmitted through an imaging lens (Achromatic, f=35 mm, B-coated) and through a 2 m long line-to-line fibre (7×105 micrometer core fibres) with seven fibres (wavelength range 400 nm-2400 nm) arranged in a straight line array. The imaging lens creates seven aperture stops by imaging the line fibre onto the sample 100, thus only allowing Raman-scattered light transmitted through these virtual aperture stops to pass through the system. The line fibre is connected to an Ibsen EAGLE Raman-s spectrometer (wave-length range 800 nm-1100 nm) coupled with an Andor iVac 316 CCD detector (sensor size of 256×2000 pixel), which images the line fibre onto the CCD such that the vertical pixels correspond to measuring positions on the sample. The detector is designed for NIR Raman, and the quantum efficiency of the detector, in the range of interest (800 nm-900 nm) for this embodiment, is 80-95%. The spectrometer and rotation stage is connected to a computer, which uses custom software to capture images from the spectrometer CCD and rotate the rotation stage. The entire measuring process is automated using the custom software, and only changes in measurement height CZ-direction) are done by hand.

Figure 2B:
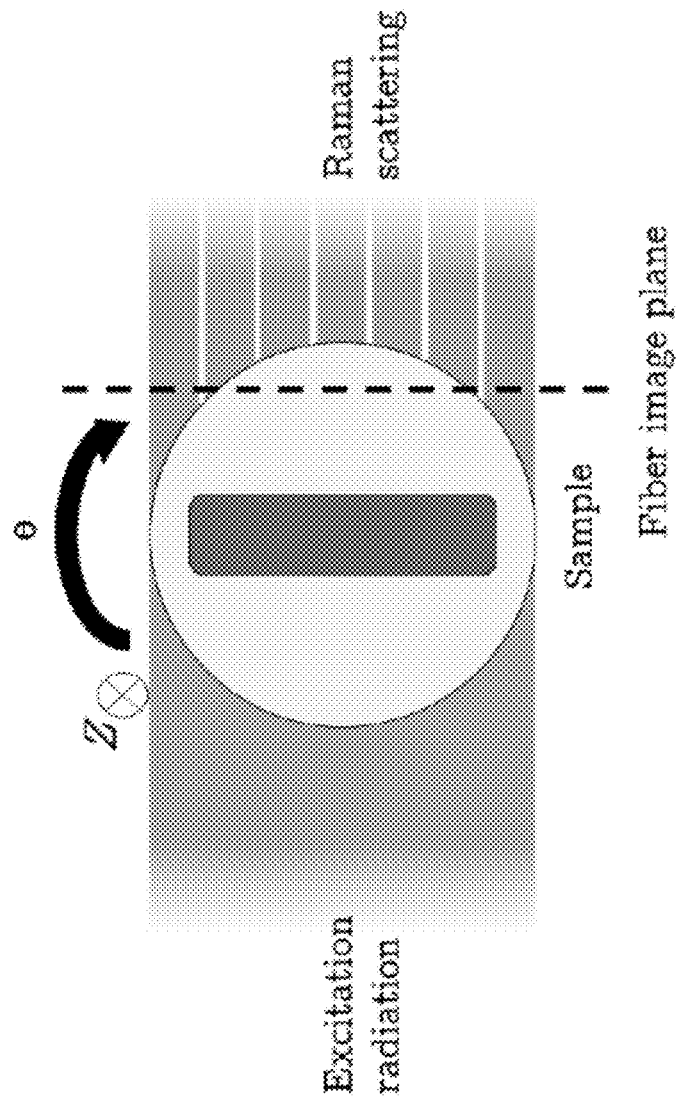

In FIG. 2B, the line array acquiring of data is schematically illustrated in a top view. The excitation laser beam (red laser) illuminates the sample. The forward scattered Raman light is collected at the image line fibre points. The sample or object is then rotated (Θ), and the measurement process is repeated. After a full rotation, the sample is moved up (lateral displacement Z) and the process is repeated.

Figure 3A:
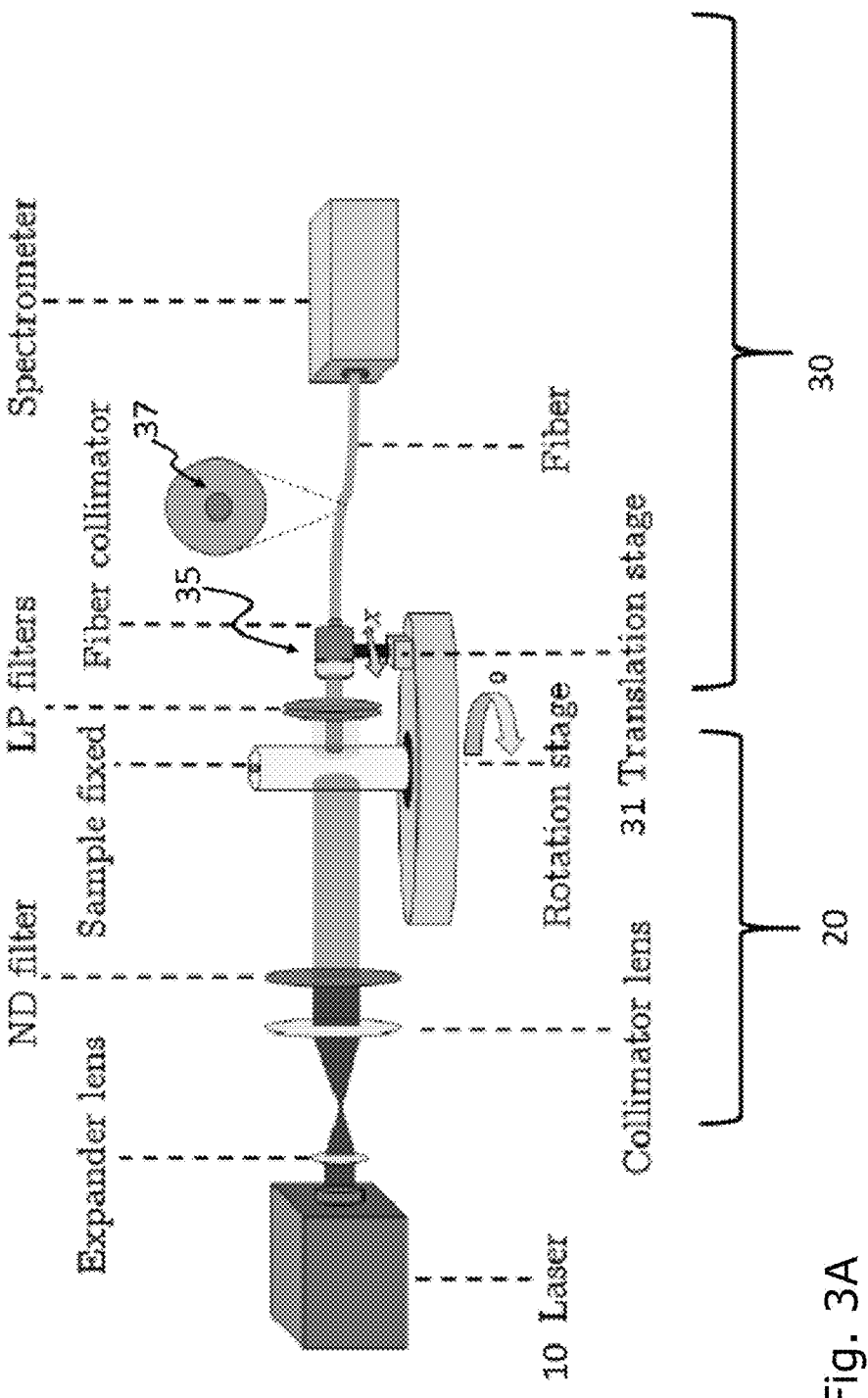
FIGS. 3A and 3B show another schematic optical system for Raman CT according to the present invention with one optical guide means being displaceable (X) in the rotational plane.

FIG. 3A shows another schematic optical system for Raman CT according to the present invention with one optical guide means being displaceable (X) in the rotational plane similar to optical in FIG. 2. However, the detector array is a point-like array 35 wherein an additional scanning (X) in a rotational plane Θ of the object is performed for acquiring multiple spectra in said two spatial dimensions. Thus, an additional translation stage 31 scans the X-dimension as shown in FIG. 3A. In this embodiment, the plurality of optical guide means may therefore be just a single fibre 37 as it will be understood by the skilled person.

Figure 3B:
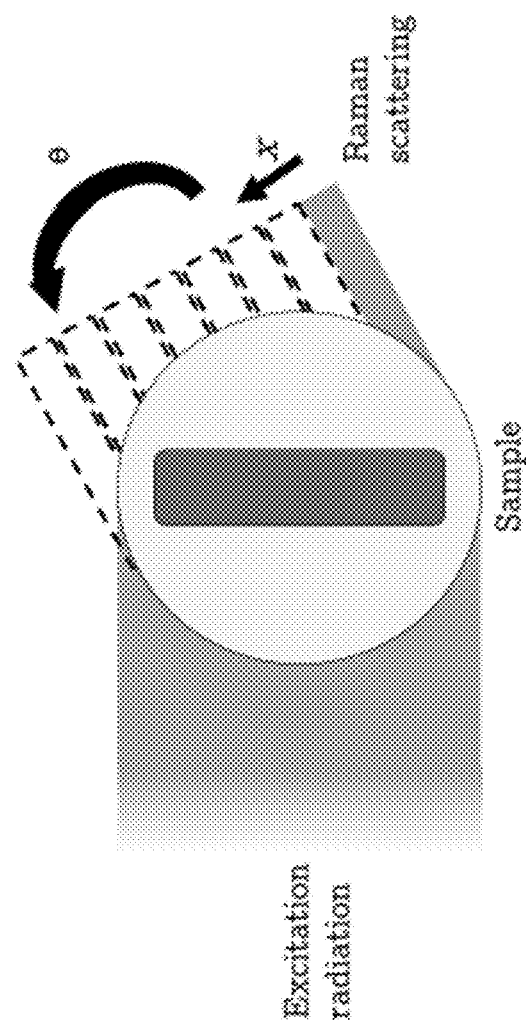

In FIG. 3B, the line array acquiring of data is schematically illustrated in a top view. During this line scan acquisition, an excitation laser beam (red) illuminates the sample, while the Raman scattering (green) is collected using a fiber collimator (not shown). The fiber is moved across (X-direction) the sample, afterwards then the collimator is rotated as indicated by the angle $\Theta$.

Figure 4:
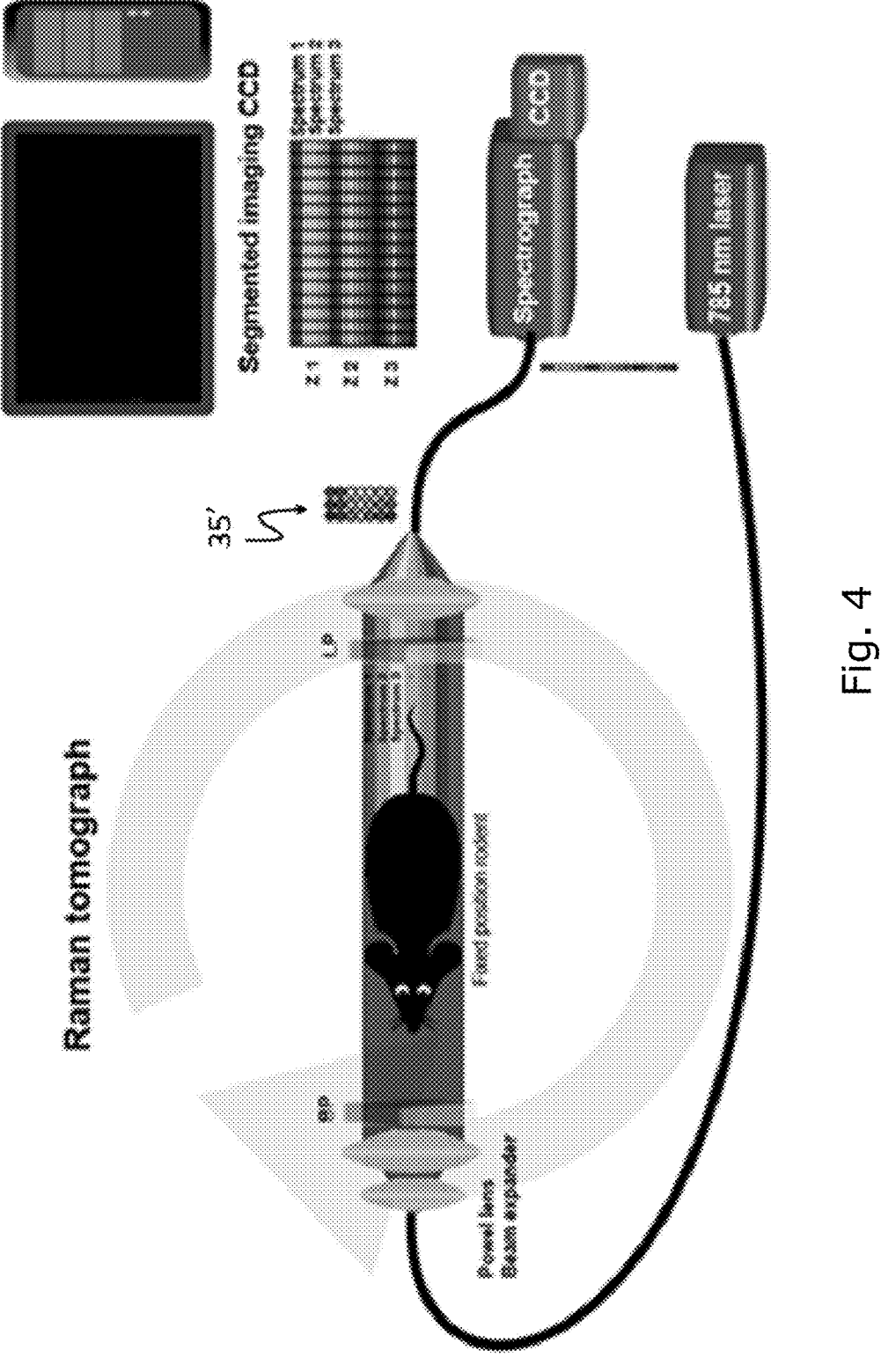
FIG. 4 shows another schematic optical system for Raman CT according to the present invention with a two-dimensional array of optical guide means.

FIG. 4 shows another schematic optical system for Raman CT according to the present invention with a two-dimensional array of optical guide means but otherwise similar to R-CT optical systems shown in FIGS. 1-3. Thus, the detector array 35' is a two-dimensional detector array wherein Raman scattered light from said object 100 is being detected by said optical receiving part by simultaneous detection in both said rotational plane ($\Theta$) and in an orthogonal (Z) dimension to said rotational plane, in this example there is recorded simultaneously three levels of the Z-dimension as schematically indicated by Z1, Z2, and Z3, but higher numbers of layers in the Z-dimension is of course possible.

This may result in faster acquisition of 3D tomographic images of objects, e.g. a rodent as shown, but more complex optics of the detector array is then a possible disadvantage. This embodiment could be relevant for a relatively larger scanning, such as scanning of humans or large animals. In particular if the imaging is performed for living animals or humans, where breathing and/or unintentional movements may disturb the imaging process. The two-dimensional detector array may have a rectangular shape, a circular shape, etc.

Figure 5A:
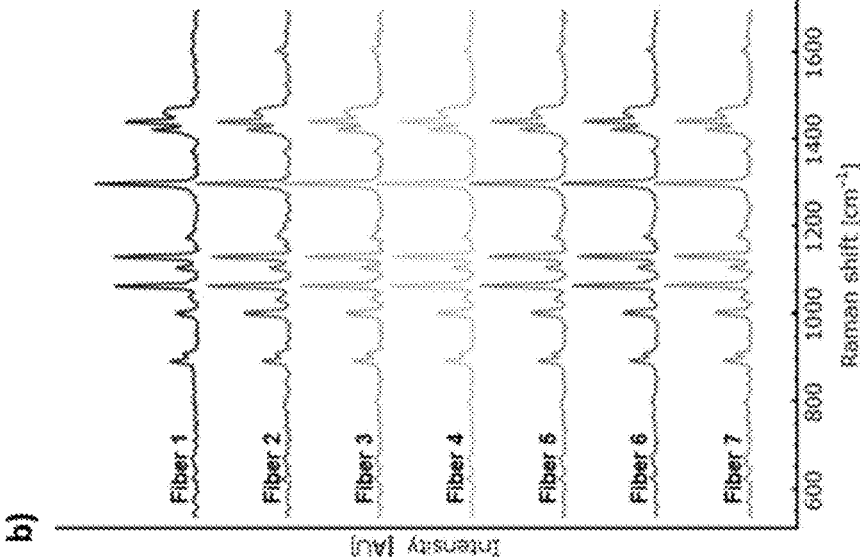
FIGS. 5A-5C show the spectra from the optical system for Raman CT seen in FIGS. 2A and 2B with an embodiment of seven optical fibres, and how the data is organised in FIG. 5C.
Figure 5B:
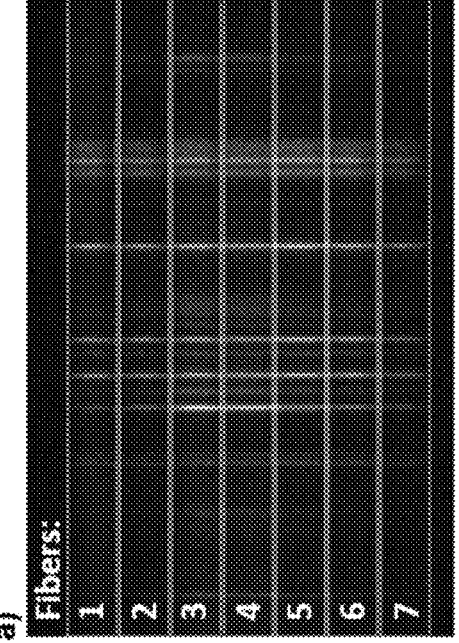
Figure 5C:
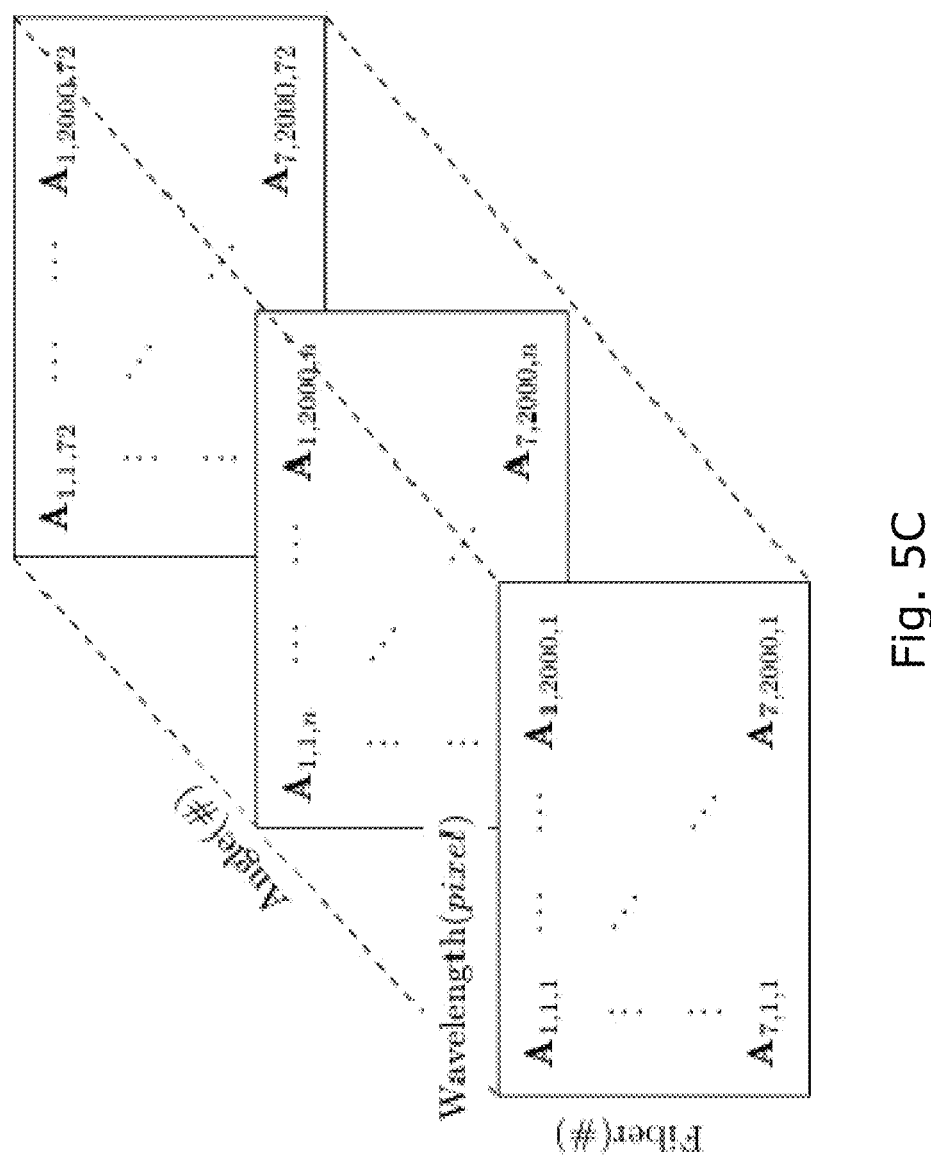

FIGS. 5A-5C show the a) CCD readout and b) extracted Raman spectra from the CCD from the optical system 1 for Raman CT seen in FIG. 2 with an embodiment of seven optical fibres, and how the data is organised in Figure SC.

A step-wise recipe for obtaining 3D reconstruction imaging for Raman CT according to the present invention may be as follows:

1. Acquire and record tomographic data from R-CT device, full CCD readout (m×n×p), where p is the number of rotations, m and n are CCD dimensions (in pixels) as indicated in Figure SC.

2. Convert pixel on CCD to wavenumber or wavelength (m×n×p) as indicated in Figure SB (on the right).

3. Map the track imaged by each fiber onto the CCD. Isolate the tracks, and perform multi-track binning on each of the tracks (7 fiber tracks in our current case; multi-track binning can also be done directly on CCD to improve readout rates). Resulting matrix (k×n×p), where k=7 tracks.

4. Unfold the datacube from 3), such that it becomes (k*p×n).

5. Smooth each multi-track binned spectra from 3) using the unfolded datacube from 4), with a second order Savitzky-Golay filter.

6. On the matrix from 5), remove baseline using a Whittaker filter.

7. Vector normalize all fiber spectra from 6).

8. Use the (still unfolded) datamatrix from 7) to run a single value decomposition (SVD). Choose the first 15 right singular vectors.

9. Select band targets. For instance, a peak specific to polystyrene PS, and a peak specific to stearic acid SA.

10. Use simulated annealing to solve the optimization problem (entropy minimization), given the selected band targets.

11. Reconstruct the 'pure' spectra from the chosen right singular vectors, and the weights calculated using band targeting entropy minimization (BTEM) in 10).

12. Re-fold the datamatrix from 7).

13. For each angle of rotation in the folded datacube from 12), (which should be k×n×p, where p is the number of rotations), calculate the weight (abundance value) of the entropically minimized reconstructed spectra from 11), using non-negativity constrained least squares fitting on each individual fiber-spectra in the datacube from 12).

14. Create a matrix (k×p) for each material, where the abundance value of a material in a given fiber (k) is noted in columns. Each column (p), corresponds to a rotation.

15. Use inverse radon transforms to back-project spectrally-derived intensity scores.

16. For 3D reconstructions loop iteratively through steps 1-15) again for each new layer in the Z-direction, where after each image reconstruction layer in 15) are placed in a combined datacube for each material.

17. Render the datacube from 16).

Figure 6:
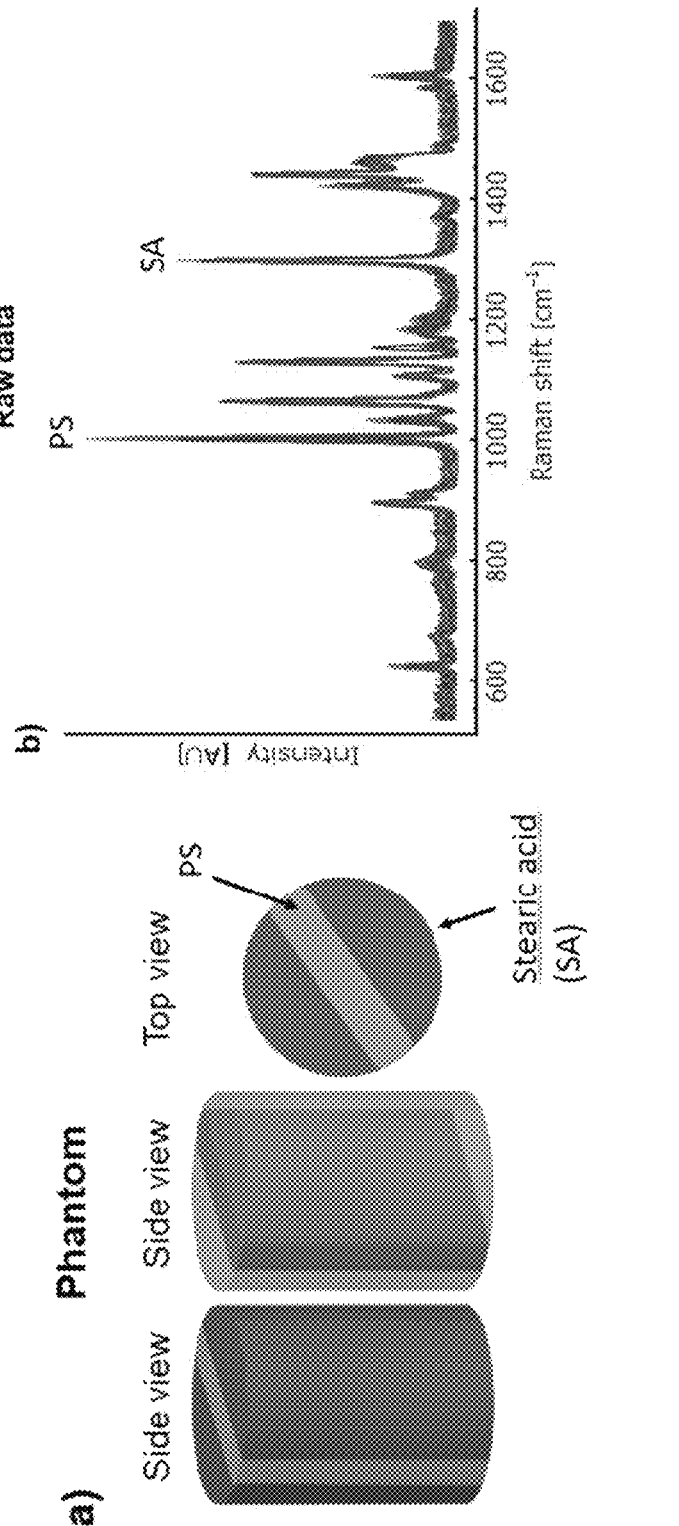
FIG. 6 shows the phantom sample with a composition of polystyrene (PS) and stearic acid (SA) and their superimposed corresponding Raman spectra.

FIG. 6 shows an illustrative a) phantom sample with a composition of polystyrene PS and stearic acid SA and b) their superimposed corresponding Raman spectra with the PS peak and SA peak used in the 3D rendering into a tomographic imaging of the phantom sample, or generally the object being tomographically imaged. The sample used is a piece of rectangular polystyrene PS 30×9×2 mm encased in a stearic acid SA cylinder 30×10 mm, roughly the size of a small little finger. Polystyrene and stearic acid both have Raman peaks in the same region (800 nm-900 nm using a 785 nm excitation laser) which simplifies the reconstruction algorithm.

Figure 7:
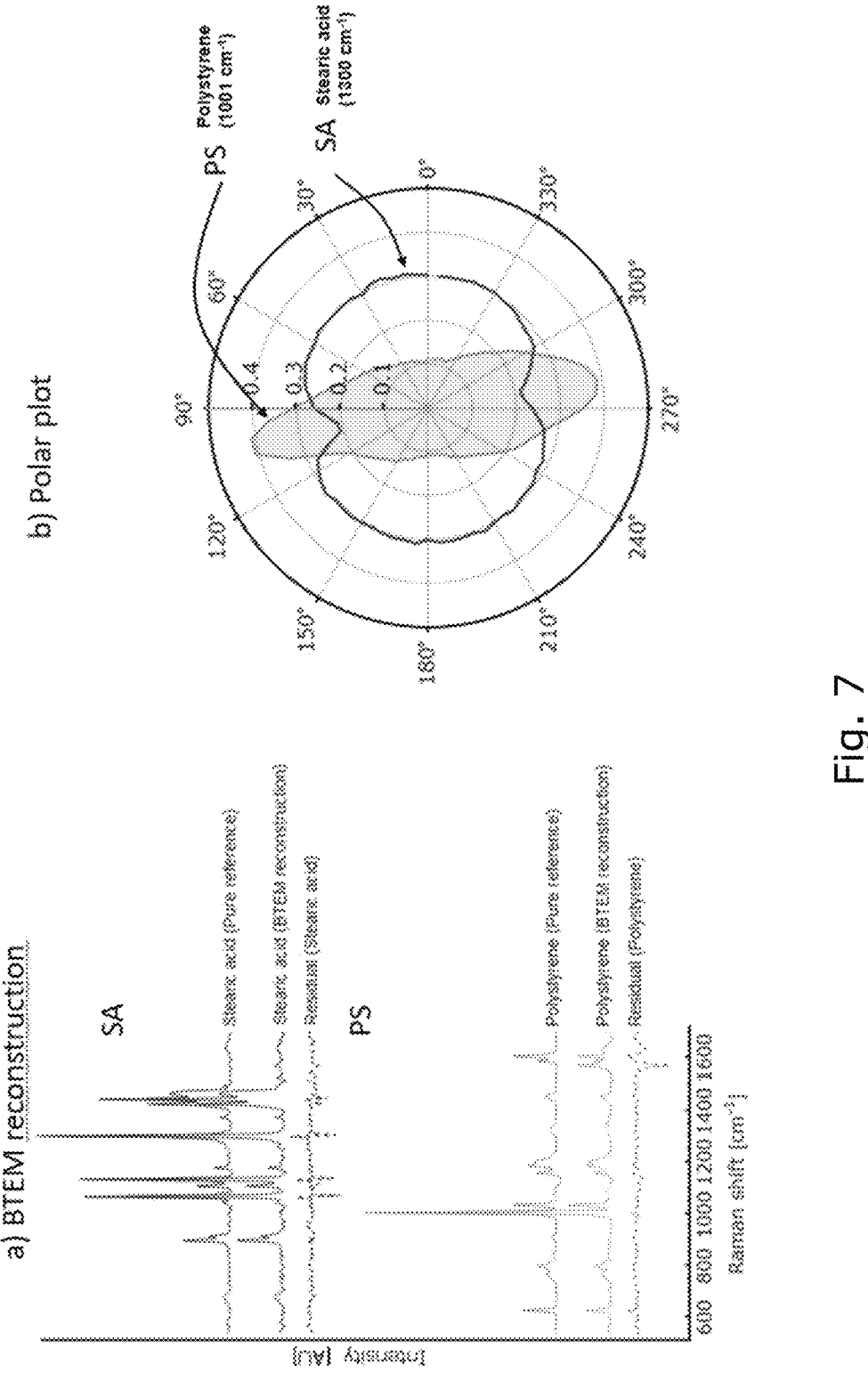
FIG. 7 shows a) the BTEM reconstruction of the PS and the SA, and b) the polar plot ($\Theta$) of the PS and SA components.

FIG. 7 shows likewise a) the band targeting entropy minimization (BTEM) reconstruction of the PS and the SA spectra described above for the phantom sample shown in FIG. 6, and b) the corresponding polar plot $\Theta$ of the PS and SA components with laser beam irradiation entering at 180 degrees and detecting with the detector array at 0 degrees. Thus, as clearly seen in FIG. 7 *b*), the Raman scattered light from the phantom sample detected by the optical receiving part of the present invention, i.e. the detector array and connected optical guide means, such as seven optical fibres, displays an anisotropic polar plot, i.e. being different in the various directions, as a function of said relative rotational position $\Theta$ corresponding to the internal spatial structure of said object.

FIGS. 8A and 8B show the 3D reconstructed tomographic image of the phantom sample with Figure SA being in full colour and FIG. 8B being the same figure but in greyscale. The original phantom sample is clearly visible and confirms that Raman CT for macroscopic objects is certainly possible.

Figure 9:
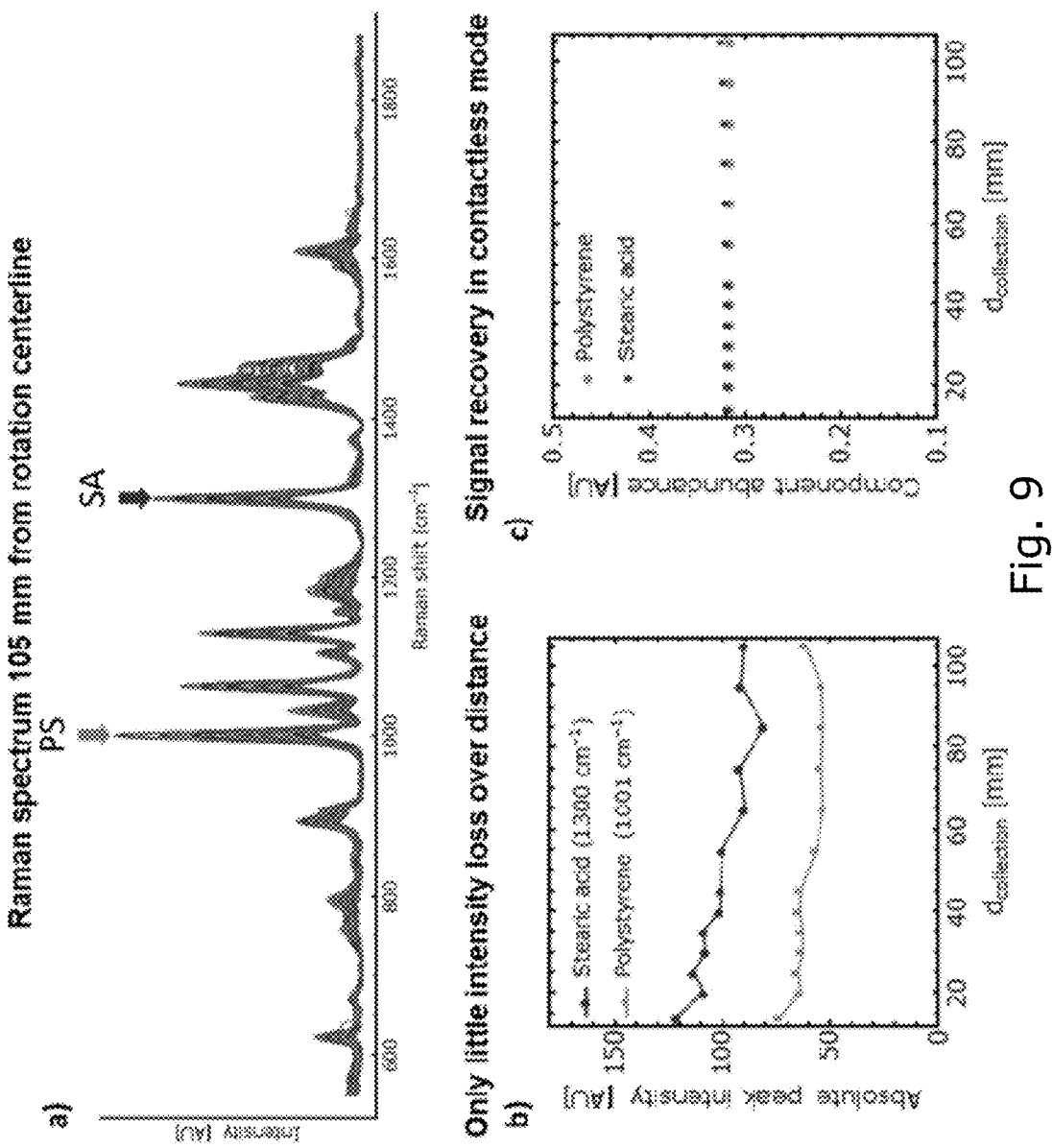
FIG. 9 is a spectra at a distance of 105 mm and two graphs showing the signal for the PS and the SA component as a function of collection distance d.

FIG. 9 is a Raman spectra at a distance of 105 mm from the sample showing that Raman scattered light is possible to detect at the far field. Similar results have been obtained even at 300 mm distance and higher. Thus, the detector array can be positioned at some distance from the object, which may facilitate simple and flexible optical detector configurations for future Raman CT within the teaching and principle of the present invention. Below two graphs show the Raman signal for the PS and the SA components, respectively, as a function of collection distanced; graph b) showing absolute intensity for both SA and PS with little dependency on the distance despite the solid angle decreasing with distance (and with same detector array), and graph c) showing the component abundance also being substantially constant as a function of the distance from the sample 100 to the detector array 35. Component abundance is measure of the weight that these two components contribute to the mixed spectra. It is noteworthy that the PS and SA does not significantly change their component abundance over the measured distance as seen in FIG. 9 $c$).

FIGS. 10A and 10B show the 3D reconstructed tomographic image of the phantom like in FIGS. 8A and 8B with two polar stepping angles of 5 and 10 degrees, respectively, FIG. 10A being full colour and FIG. 10B is the same figure but in greyscale. This experiment is performed to test the dependency of the polar angle Θ. It is to be expected that the 3D image is better for 5 degrees step size of the rotational angle Θ, but still 10 degrees step size yields an acceptable spatial resolution of the phantom sample in this early demonstration of Raman CT.

Figure 11:
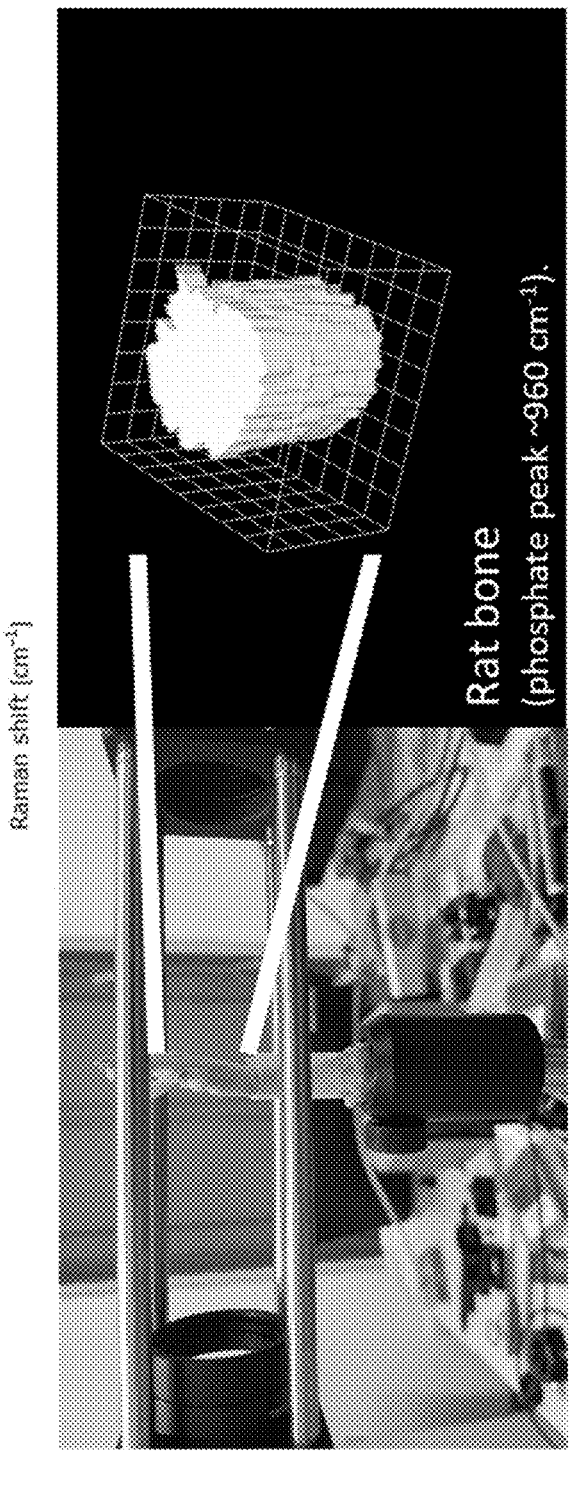
FIG. 11 shows Raman spectra from a rat leg, a photograph of the rat leg in the optical system and the corresponding 3D reconstructed polar image of the bone.

FIG. 11 shows Raman spectra from a rat leg with indications of the various Raman peaks seen, e.g. phosphate around 960 cm−1 from the bone and amide groups from soft tissue, a photograph (lower left) of the rat leg (still with fur and skin) vertically positioned and fixated in the optical system 1 and the corresponding 3D reconstructed polar image of the rat leg (lower right) with the rat bone structure clearly visible in this coarse resolution with only 5 layers in the lateral Z-dimension. Due to the low resolution at this early stage of development of the invention, the spatial resolution of the 3D rendering is still arbitrary, but more measurements will expectedly yield at least the same spatial resolution as for the phantom sample, and therefore the possibility to differentiate the various kind of soft tissue in the rat leg. A rat leg can be used as a model for anti-arthritic treatment and other illnesses. The rat leg was measured at a distance of 340 mm from sample to detector array, again supporting that relatively remote measurement of Raman spectra is possible.

Figure 12:
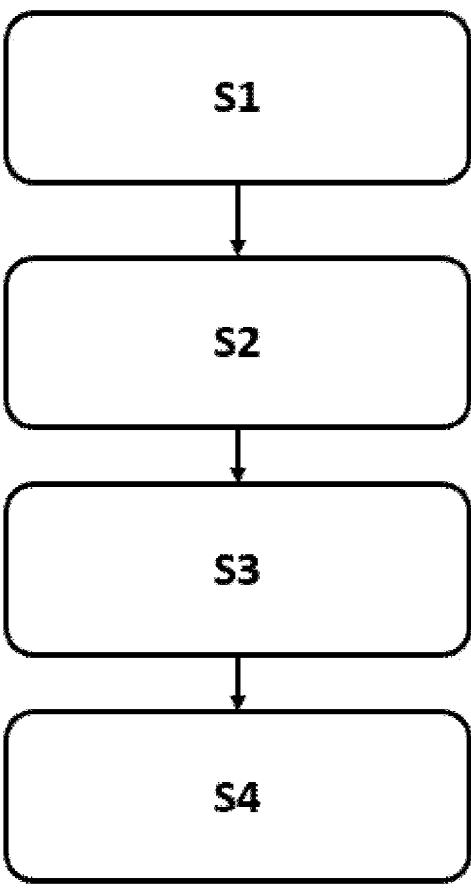
FIG. 12 is a schematic system-chart representing an out-line of a method according to the invention.

FIG. 12 is a schematic system-chart representing an out-line of a method according to the invention for optical tomography scanning for 3D imaging of an object 100, such as non-invasive 3D imaging of, at least part of, a patient or an animal, using Raman scattered light from said object, said method comprising:

S1 providing a monochromatic light source 10, cf. FIGS. 1-4, arranged for illuminating said object, S2 fixating in an optical configuration 20 said object, said optical configuration being arranged for rotating to a plurality of relative rotational positions Θ between said object and an optical tomography scanning system 1, cf. FIGS. 1-4, S3 arranging an optical receiving part 30 optically relative to said object for receiving Raman scattered light from said object, the optical receiving part comprising:

a detector array 35 or 35' arranged for receiving the Raman scattered light in two spatial dimensions, and a plurality of optical guide means 37, such as optical fibres, arranged for receiving and conveying further said Raman scattered light to a spectrometer 38 for recording into multiple spectra upon acquiring in said two spatial dimensions, X and/or Z, for each relative rotational position Θ of said object, and S4 providing a processing part 40, such as a connected computer, for 3D image reconstruction of said object based on said recorded multiple spectra based on a plurality of relative rotational positions Θ of said object.

FIGS. 13A and 13B show a 3D reconstructed tomographic images from a rat leg. FIG. 13A being full colour and FIG. 13B is the same figure but in greyscale. The graph in FIGS. 13A and 13B shows Raman spectra for bone and for soft tissue. These are cleaned Raman spectra unlike the Raman spectra in FIG. 11, where the measured Raman spectra contains all the recorded information. In FIGS. 13A and 13B multivariate analysis has been used to separate bone relevant data and soft tissue relevant data into two separate spectre. The pictures in FIGS. 13A and 13B show the rat leg, a soft tissue image reconstruction, a bone image reconstruction, a combined soft tissue reconstruction and a fluorescence image. The fluorescence image is based on reflections from natural occurring fluorescence substance in the rat leg. The fluorescence data is usually removed from the data before the tomographic reconstruction of bone and soft tissue. However the fluorescence data can also be used to reconstruct an image as shown. This image however do not contain any chemical information but only spatial information.

In short, the invention relates to an optical tomography scanning system 1 for 3D imaging of an object 100, for example an experimental rodent or a patient, using Raman scattered light from the object. A laser 10 and an optical configuration 20 for fixating the object and arranged for rotation Θ is provided, and an optical receiving part 30 receives Raman scattered light. The optical receiving part has a detector array 35 for receiving the Raman scattered light in two spatial dimensions, X and/or Z, and optical guide means 37 convey Raman scattered light to a spectrometer 38, where multiple spectra are recorded for the two spatial dimensions for each relative rotational position Θ of the object. A 3D image reconstruction of the object based on the multiple spectra at a plurality of relative rotational positions Θ of the object enables 3D tomographic imaging of the object, such as an experimental rat, cf. FIG. 1.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

In other embodiments, the present invention also relates to:

1. An optical tomography scanning system (1) for 3D imaging of an associated object (100), such as non-invasive 3D imaging of, at least part of, a patient or an animal, using Raman scattered light from said object, said system comprising:

a monochromatic light source (10) arranged for illuminating said object, an optical configuration (20) for fixating said object and arranged for rotating to a plurality of relative rotational positions (Θ) between said object and the optical tomography scanning system, an optical receiving part (30) optically arranged relative to said object for receiving Raman scattered light from said object, the optical receiving part comprising:

a detector array (35, 35') arranged for receiving the Raman scattered light in two spatial dimensions (X, Z), and a plurality of optical guide means (37) arranged for receiving and conveying further said Raman scattered light to a spectrometer (38) for recording into multiple spectra upon acquiring in said two spatial dimensions for each relative rotational position (Θ) of said object, and a processing part (40) arranged for 3D image reconstruction of said object based on said recorded multiple spectra based on a plurality of relative rotational positions (Θ) of said object.

2. The optical tomography scanning system according to embodiment 1, wherein the scattered light from said object detected by said optical receiving part displays constructive interference near, or at, the detector array, preferably said detector array being located approximately at least 5, 10, 15, 20, 25, 30 cm from said object.

3. The optical tomography scanning system according to any of the preceding embodiments, wherein the scattered light from said object detected by said optical receiving part displays an anisotropic polar plot as a function of said relative rotational position (Θ) corresponding to the internal spatial structure of said object.

4. The optical tomography scanning system according to embodiment 1, wherein said optical configuration for fixating said object is further arranged for performing a relative longitudinal displacement (z) of said object, said longitudinal displacement being substantially orthogonal to a rotational plane of said relative rotation (Θ) between said object and the optical tomography scanning system.

5. The optical tomography scanning system according to any of the preceding embodiments, wherein the tomography scanning is simultaneously obtaining corresponding spectral information and spatial information about said object.

6. The optical tomography scanning system according to any of the preceding embodiments, wherein the tomography scanning is based on backward-projection (BP) type measurements of the Raman scattered light in said optical receiving part.

7. The optical tomography scanning system according to any of the preceding embodiments, wherein the Raman scattered light from said object being detected by said optical receiving part is forward scattered.

8. The optical tomography scanning system according to embodiment 4, wherein said detector array (35) is a line array wherein the plurality of optical guide means are arranged substantially in a rotational plane (Θ) of the object.

9. The optical tomography scanning system according to embodiment 4, wherein said detector array (35) is a point-like array wherein an additional scanning (X) in a rotational plane (Θ) of the object is performed for acquiring multiple spectra in said two spatial dimensions.

10. The optical tomography scanning system according to embodiment 1, wherein said detector array (35') is a two-dimensional detector array wherein Raman scattered light from said object is being detected by said optical receiving part by simultaneous detection in both said rotational plane (Θ) and in an orthogonal (Z) dimension to said rotational plane.

11. The optical tomography scanning system according to any of the preceding embodiments, wherein the detector array and the corresponding optical guide means are mutually arranged for conveying a Raman spectrum in each optical guide means (37), preferably each optical guide means comprises an optical fiber capable of conveying a Raman spectrum from said object.

12. The optical tomography scanning system according to any of the preceding embodiments, wherein the 3D image reconstruction is performed using: a spectral unmixing technique, a spectral Library supervised reconstruction, an information entropy minimization technique, such as BTEM (band target entropy minimization), a multivariate curve resolution (MCR) technique, a vertex component analysis (VCA) technique, N-FINDR, a principal component analysis (PCA) technique, or any combinations thereof.

13. The optical tomography scanning system according to any of the preceding embodiments, wherein the object is an animal body or a patient body, or part thereof, and the 3D image reconstruction is capable of resolving said spectral information and spatial information so as to provide a tissue differentiating resolution in the 3D image construction.

14. A method for optical tomography scanning for 3D imaging of an object (100), such as non-invasive 3D imaging of, at least part of, a patient or an animal, using Raman scattered light from said object, said method comprising:

providing a monochromatic light source (10) arranged for illuminating said object, fixating in an optical configuration (20) said object, said optical configuration being arranged for rotating to a plurality of relative rotational positions (Θ) between said object and an optical tomography scanning system (1), arranging an optical receiving part (30) optically relative to said object for receiving Raman scattered light from said object, the optical receiving part comprising:

a detector array (35, 35') arranged for receiving the Raman scattered light in two spatial dimensions, and a plurality of optical guide means (37) arranged for receiving and conveying further said Raman scattered light to a spectrometer (38) for recording into multiple spectra upon acquiring in said two spatial dimensions (X, Z) for each relative rotational position (Θ) of said object, and providing a processing part (40) for 3D image reconstruction of said object based on said recorded multiple spectra based on a plurality of relative rotational positions (Θ) of said object.

The invention claimed is:

1. An optical tomography scanning system for three-dimensional (3D) imaging of an associated object using Raman scattered light from said object, said system comprising:

a monochromatic light source configured to illuminate said object, a mounting apparatus for fixating said object and configured to rotate said object to a plurality of relative rotational positions (Θ) between said object and the optical tomography scanning system, an optical receiving part configured to be optically arranged relative to said object for receiving Raman scattered light from said object, the optical receiving part comprising:

a detector array configured to receive the Raman scattered light in two spatial dimensions (X, Z), and a plurality of optical guides configured to receive and convey said Raman scattered light to a spectrometer configured to record, using said Raman scattered light, multiple non-time-resolved spectra in said two spatial dimensions for each relative rotational position (Θ) of said object, wherein the Raman scattered light from said object detected by said optical receiving part has an anisotropic intensity distribution as a function of said relative rotational position (Θ), said anisotropic intensity distribution corresponding to an internal spatial structure of said object, and a processor configured to generate a 3D image of said object based on said recorded multiple non-time-resolved spectra for the plurality of relative rotational positions (Θ) of said object, thereby using said function of said relative rotational position (Θ) corresponding to the internal spatial structure of said object.

2. The optical tomography scanning system according to claim 1, wherein said object is an animal body or a patient body, or part thereof, and wherein the mounting apparatus is configured to fixate the animal body or patient body, or part thereof, relative to the optical tomography scanning system.

3. The optical tomography scanning system according to claim 1, wherein said mounting apparatus is configured to locate said detector array approximately at least 5 cm and up to approximately 34 cm from said object.

4. The optical tomography scanning system according to claim 1, wherein said mounting apparatus for fixating said object is further configured to perform a relative longitudinal displacement (Z) of said object, said longitudinal displacement being substantially orthogonal to a rotational plane of said relative rotation (Θ) between said object and the optical tomography scanning system.

5. The optical tomography scanning system according to claim 4, wherein said detector array is a line array, wherein the plurality of optical guides are configured to be arranged substantially in a rotational plane (Θ) of the object.

6. The optical tomography scanning system according to claim 4, wherein said detector array is a point-like array, wherein the system is configured to perform a scanning (X) in a rotational plane (Θ) of the object for acquiring multiple spectra in said two spatial dimensions.

7. The optical tomography scanning system according to claim 1, wherein the processor is further configured to select a waveband corresponding to a peak associated with one of a plurality of materials present in said object, and to generate the 3D image based at least in part on the selected waveband.

8. The optical tomography scanning system according to claim 1, wherein the processor is configured to generate the 3D image of said object by at least performing tomographic backward-projection (BP) based on the Raman scattered light in said optical receiving part.

9. The optical tomography scanning system according to claim 1, wherein said optical receiving part is arranged to receive forward scattered light from said object.

10. The optical tomography scanning system according to claim 1, wherein said detector array is a two-dimensional detector array, wherein said optical receiving part is configured to simultaneously detect the Raman scattered light from said object in both said rotational plane (Θ) and in an orthogonal (Z) dimension to said rotational plane.

11. The optical tomography scanning system according to claim 1, wherein the detector array and the corresponding optical guides are mutually arranged for conveying a Raman spectrum in each of the optical guides.

12. The optical tomography scanning system according to claim 11, wherein each of the optical guides comprises an optical fiber capable of conveying a Raman spectrum from said object.

13. The optical tomography scanning system according to claim 1, wherein the 3D image is generated using: a spectral unmixing technique, a spectral Library supervised reconstruction, an information entropy minimization technique, band target entropy minimization (BTEM), a multivariate curve resolution (MCR) technique, a vertex component analysis (VCA) technique, N-FINDR, a principal component analysis (PCA) technique, or any combinations thereof.

14. The optical tomography scanning system according to claim 1, wherein the monochromatic light source comprises a laser source, the system further comprising a multimode optical fiber positioned to receive light from the laser source.

15. A method for optical tomography scanning for three-dimensional (3D) imaging of an object using Raman scattered light from said object, said method comprising:

providing a monochromatic light source configured to illuminate said object, fixating said object in a mounting apparatus, said mounting apparatus being configured to rotate said object to a plurality of relative rotational positions (θ) between said object and an optical tomography scanning system, arranging an optical receiving part optically relative to said object for receiving Raman scattered light from said object, the optical receiving part comprising:

a detector array configured to receive the Raman scattered light in two spatial dimensions, and a plurality of optical guides configured to receive and convey said Raman scattered light to a spectrometer configured to record, using said Raman scattered light, multiple non-time-resolved spectra in said two spatial dimensions (X, Z) for each relative rotational position (Θ) of said object, and wherein the Raman scattered light from said object detected by said optical receiving part has an anisotropic intensity distribution as a function of said relative rotational position (Θ) corresponding to the internal spatial structure of said object, and providing a processor configured to generate a 3D image reconstruction of said object by at least performing tomographic backward-projection based on said recorded multiple non-time-resolved spectra based on the plurality of relative rotational positions (Θ) of said object, thereby using said function of said relative rotational position (Θ) corresponding to the internal spatial structure of said object.

16. The method according to claim 15, wherein the processor is further configured to select a waveband corresponding to a peak associated with one of a plurality of materials present in said object, and to generate the 3D image reconstruction based at least in part on the selected waveband.

* * * * *